US010241034B2

(12) United States Patent
Sugawa et al.

(10) Patent No.: US 10,241,034 B2
(45) Date of Patent: Mar. 26, 2019

(54) CONCENTRATION MEASURING METHOD

(71) Applicant: TOHOKU UNIVERSITY, Sendai, Miyagi (JP)

(72) Inventors: Shigetoshi Sugawa, Sendai (JP); Rihito Kuroda, Sendai (JP)

(73) Assignee: TOHOKU UNIVERSITY, Sendai, Miyagi (JP)

( * ) Notice: Subject to any disclaimer, the term of this patent is extended or adjusted under 35 U.S.C. 154(b) by 131 days.

(21) Appl. No.: 15/506,440

(22) PCT Filed: Aug. 24, 2015

(86) PCT No.: PCT/JP2015/073675
§ 371 (c)(1),
(2) Date: Feb. 24, 2017

(87) PCT Pub. No.: WO2016/031750
PCT Pub. Date: Mar. 3, 2016

(65) Prior Publication Data
US 2017/0254746 A1   Sep. 7, 2017

(30) Foreign Application Priority Data

Aug. 29, 2014 (JP) ................................. 2014-176575
Feb. 23, 2015 (WO) .................. PCT/JP2015/055076

(51) Int. Cl.
*G01J 5/02* (2006.01)
*G01N 21/31* (2006.01)
*G01N 21/03* (2006.01)
*G01N 21/3504* (2014.01)
*A61B 5/145* (2006.01)
*A61B 5/1455* (2006.01)
(Continued)

(52) U.S. Cl.
CPC ........... *G01N 21/31* (2013.01); *A61B 5/1455* (2013.01); *A61B 5/14532* (2013.01);
(Continued)

(58) Field of Classification Search
CPC ............. G01N 21/031; G01N 21/3504; G01N 21/0332; G01N 2021/158; G01N 2201/08;
(Continued)

(56) References Cited

U.S. PATENT DOCUMENTS 5,015,099 A   5/1991  Nagai et al.
7,215,987 B1 *  5/2007  Sterling ............. A61B 5/14551
600/322

(Continued)

FOREIGN PATENT DOCUMENTS

JP   01-257245   10/1989
JP   03-015742   1/1991
(Continued)

Primary Examiner — Kiho Kim
(74) Attorney, Agent, or Firm — Venable LLP

(57) ABSTRACT

A concentration measurement method accurately, quickly, and non-destructively measures the concentration of a predetermined chemical component within an object to a nano-order trace concentration level in real time. A time sharing method irradiates the object light of a first wavelength and light of a second wavelength having different light absorption rates with respect to the object to be measured. Light of both wavelengths that arrives optically through the object is received by a shared light reception sensor, and signals respectively relating to light of the first and second wavelengths are output from the light reception sensor in accordance with the received light. A differential signal of these signals is formed, and the concentration of a chemical component in the object to be measured is derived on the basis of the differential signal.

20 Claims, 23 Drawing Sheets

(51) Int. Cl.
*G01N 21/35* (2014.01)
*G01N 21/15* (2006.01)
*A61B 5/00* (2006.01)
*A61B 5/11* (2006.01)
*A61B 5/1477* (2006.01)

(52) U.S. Cl.
CPC ....... *G01N 21/031* (2013.01); *G01N 21/0332* (2013.01); *G01N 21/3151* (2013.01); *G01N 21/35* (2013.01); *G01N 21/3504* (2013.01); *A61B 5/1112* (2013.01); *A61B 5/1122* (2013.01); *A61B 5/1477* (2013.01); *A61B 5/14535* (2013.01); *A61B 5/14546* (2013.01); *A61B 5/4227* (2013.01); *A61B 5/6898* (2013.01); *A61B 2505/07* (2013.01); *G01N 2021/158* (2013.01); *G01N 2021/3159* (2013.01); *G01N 2021/3181* (2013.01); *G01N 2201/08* (2013.01)

(58) Field of Classification Search
CPC .... G01N 21/31; G01N 21/3151; G01N 21/35; G01N 2021/3159
See application file for complete search history.

(56) References Cited

U.S. PATENT DOCUMENTS

| | | | |
|---|---|---|---|
| 8,085,404 | B2 | 12/2011 | Yamakage et al. |
| 2006/0118724 | A1* | 6/2006 | Nanko ................... G01N 21/37 250/343 |
| 2009/0095918 | A1* | 4/2009 | Iwase ................... G01N 21/031 250/432 R |
| 2009/0323068 | A1* | 12/2009 | Yamakage ........... G01N 21/031 356/437 |
| 2013/0171675 | A1 | 7/2013 | Tsukamoto et al. |

FOREIGN PATENT DOCUMENTS

| | | |
|---|---|---|
| JP | 2003-114191 | 4/2003 |
| JP | 2006-141712 | 6/2006 |
| JP | 2006-324532 | 11/2006 |
| JP | 2008-051598 | 3/2008 |
| JP | 2008-256398 | 10/2008 |
| JP | 2010-109304 | 5/2010 |
| JP | 2012-137500 | 7/2012 |
| JP | 2012-138407 | 7/2012 |

* cited by examiner

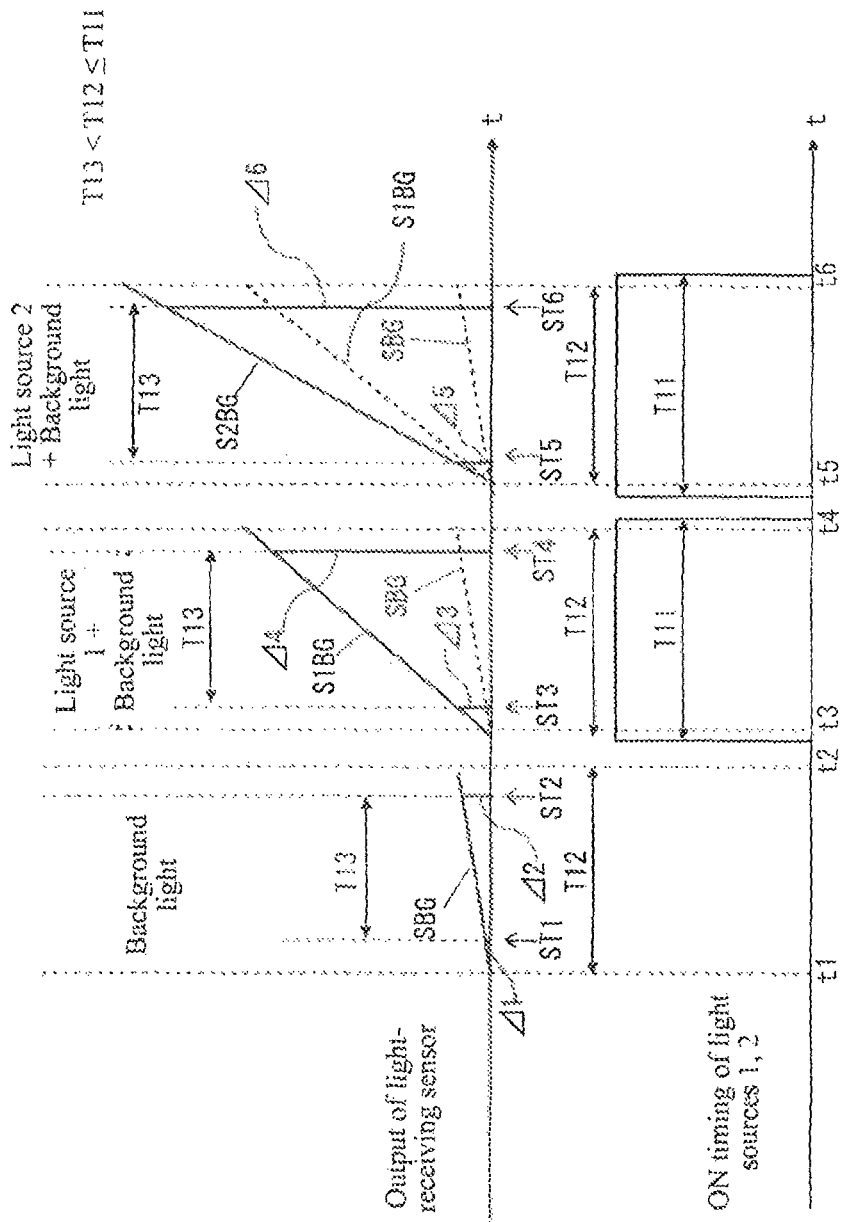
[Fig. 1]

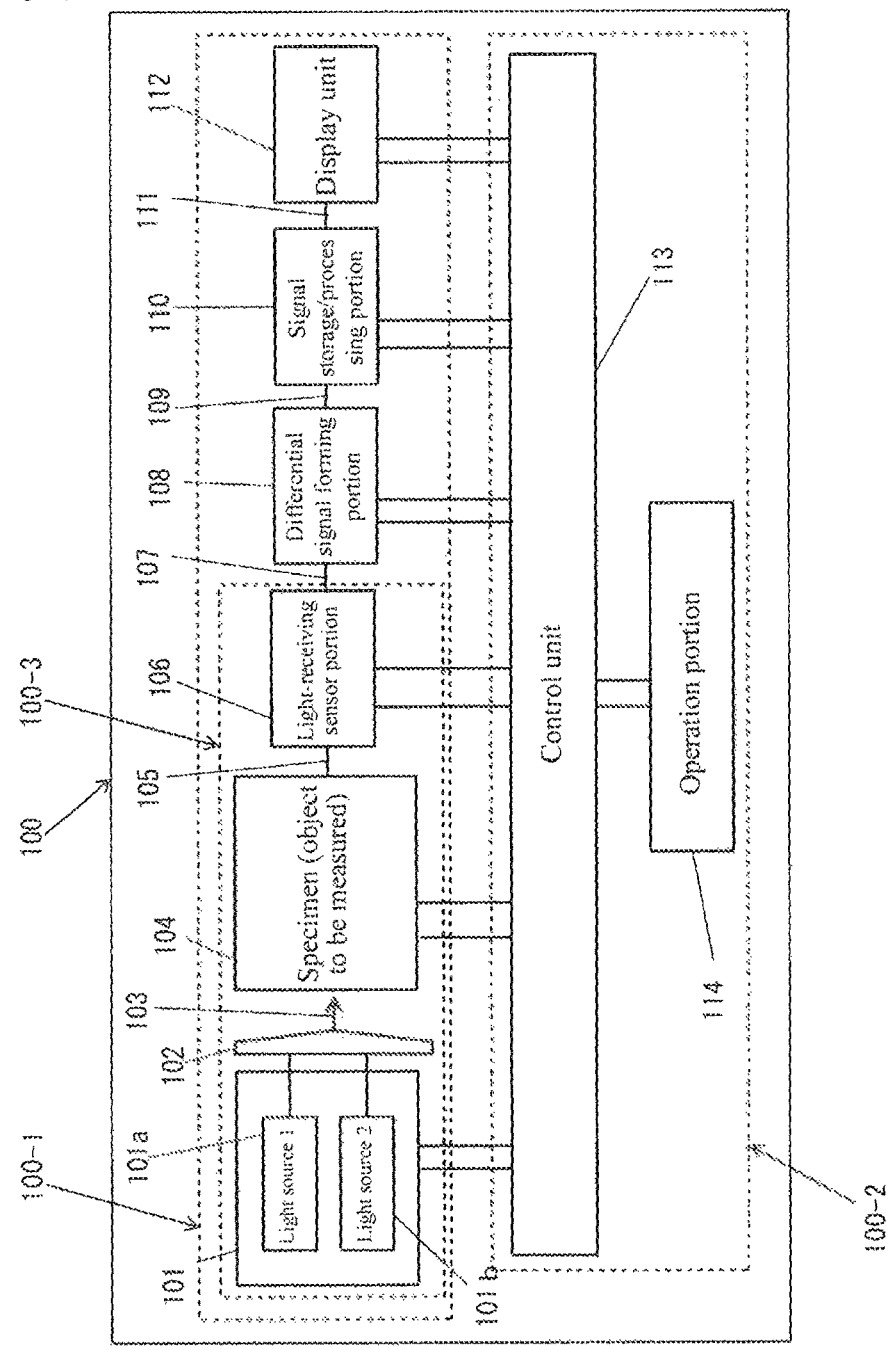
[Fig. 2]

[Fig. 3]
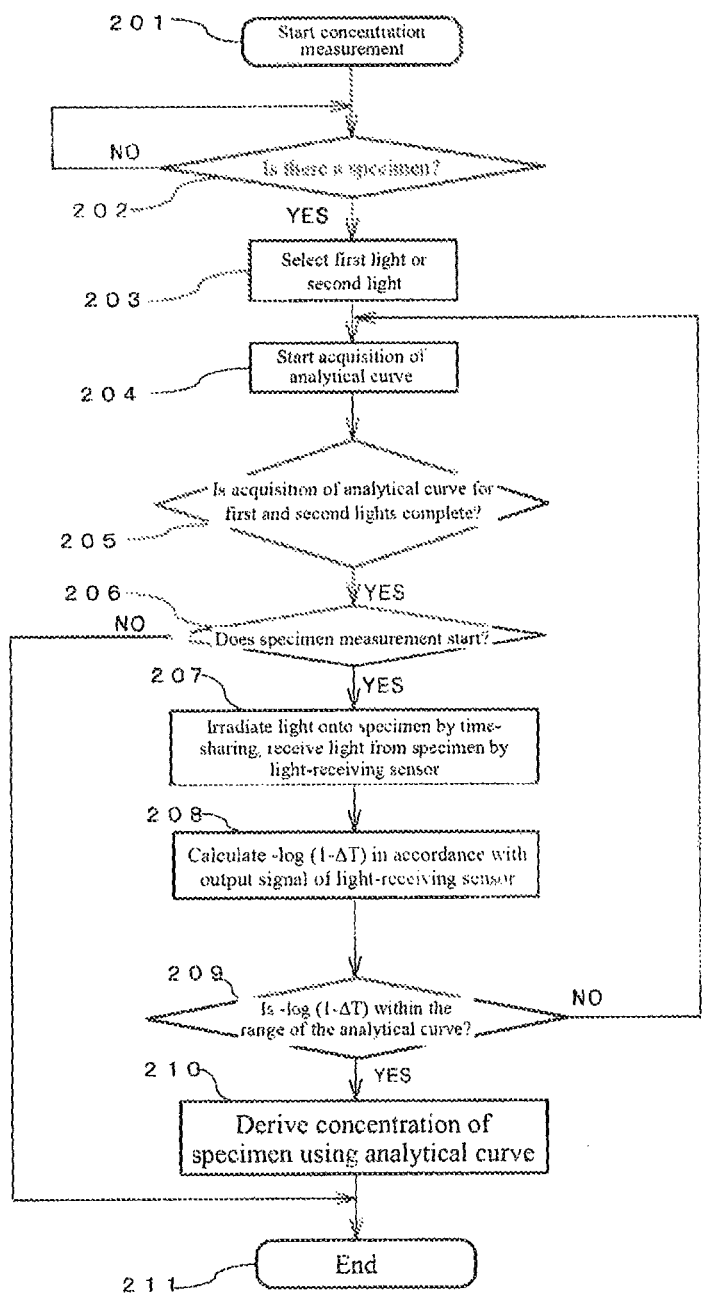

[Fig. 4]
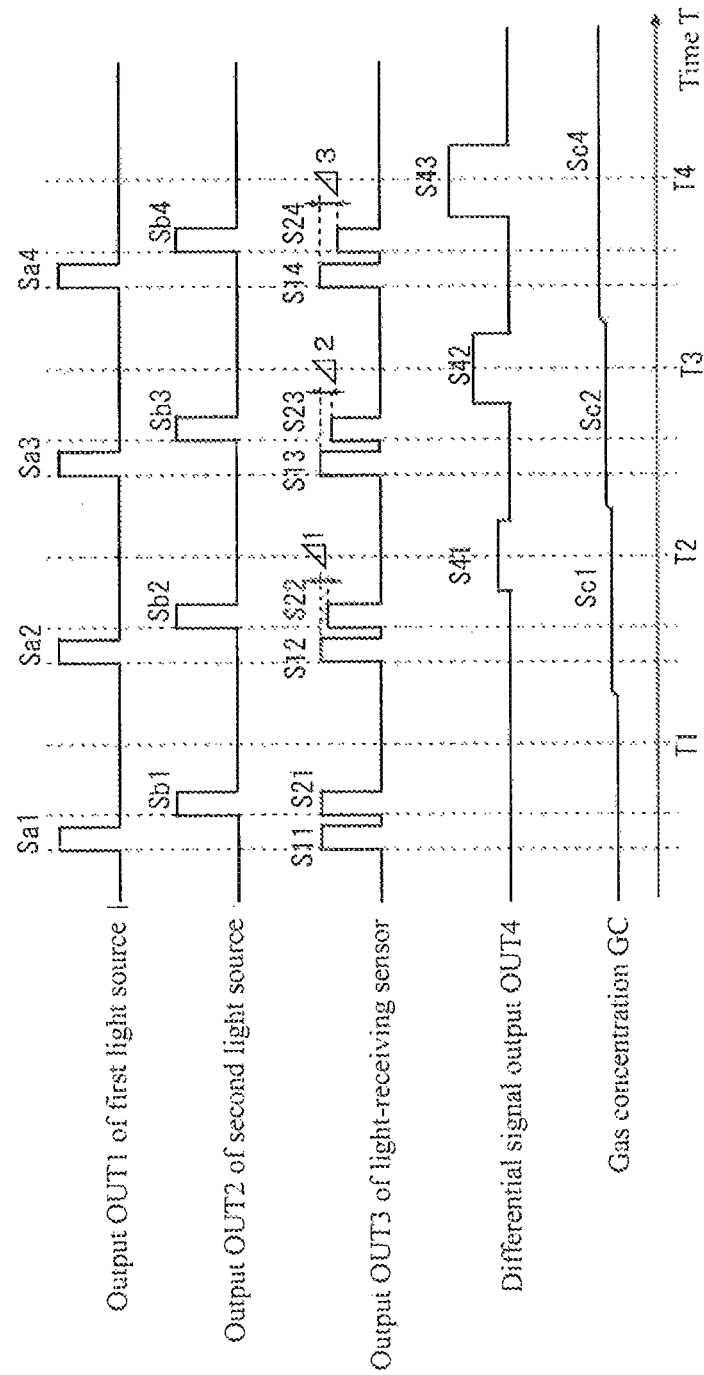

[Fig. 5]
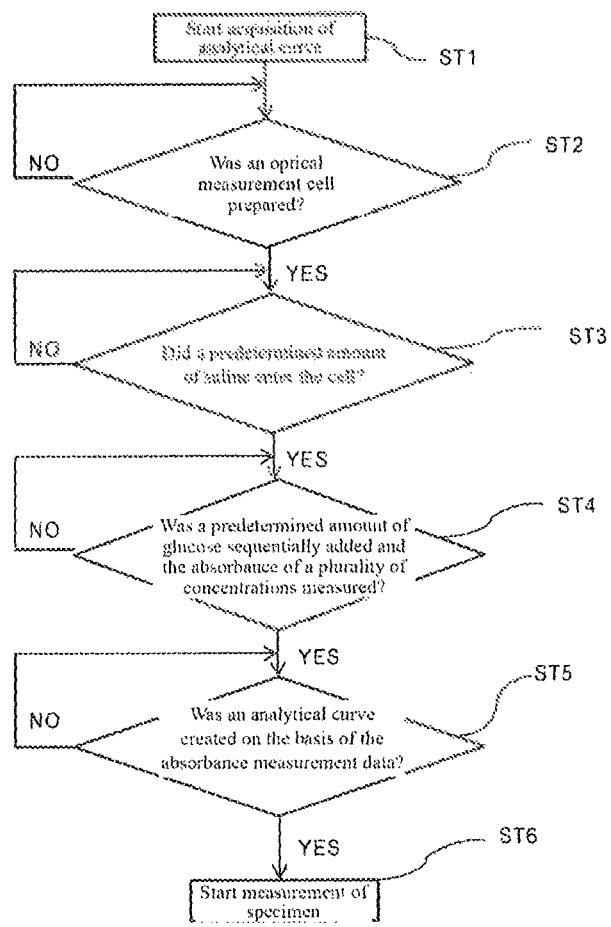

[Fig. 6]
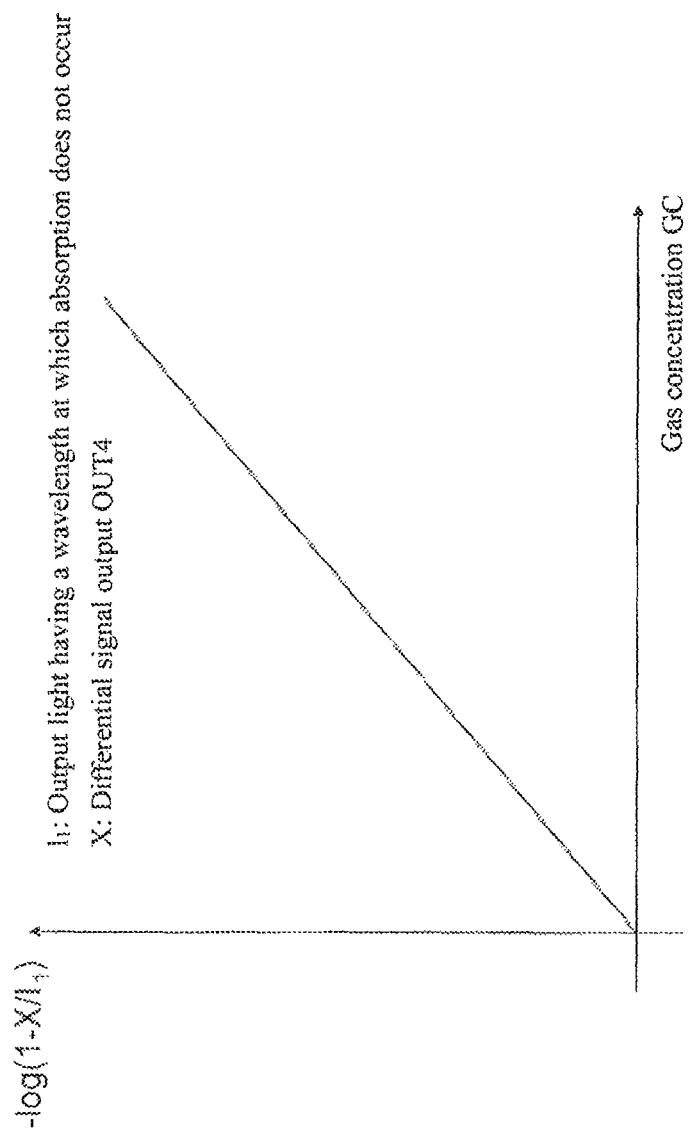

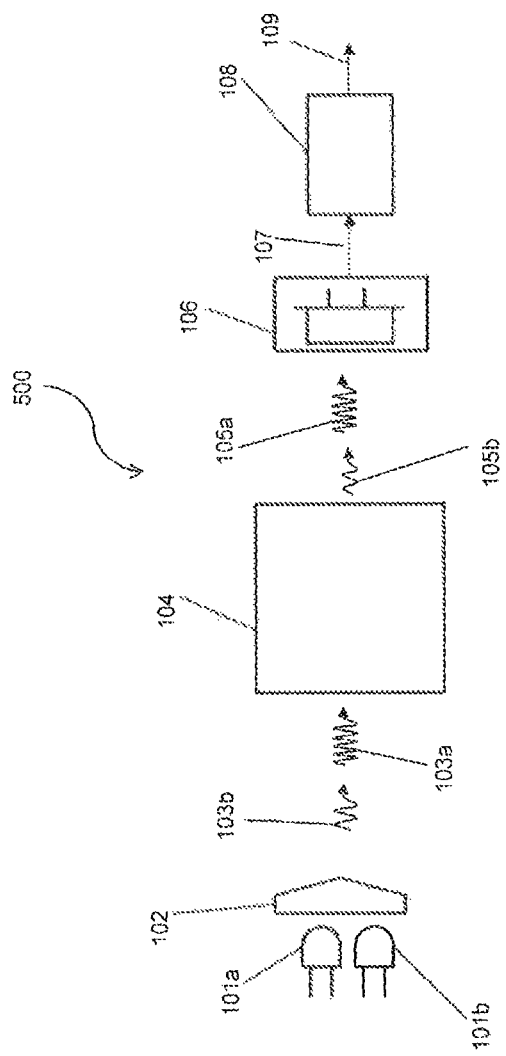
[Fig. 7]

[Fig. 8]
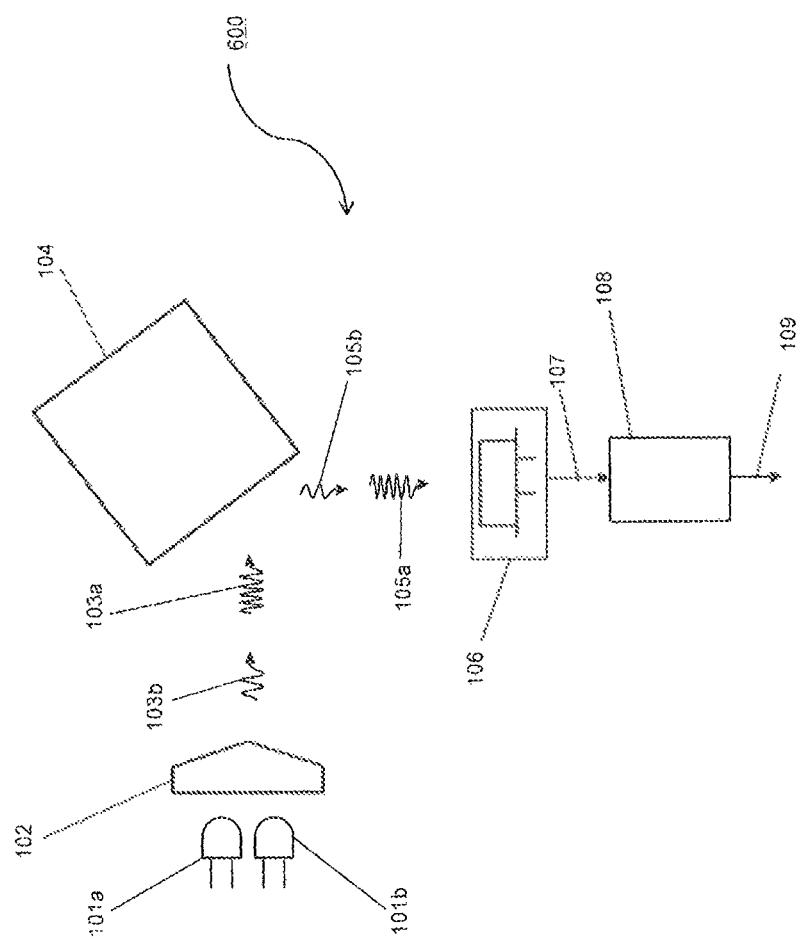

[Fig. 9]
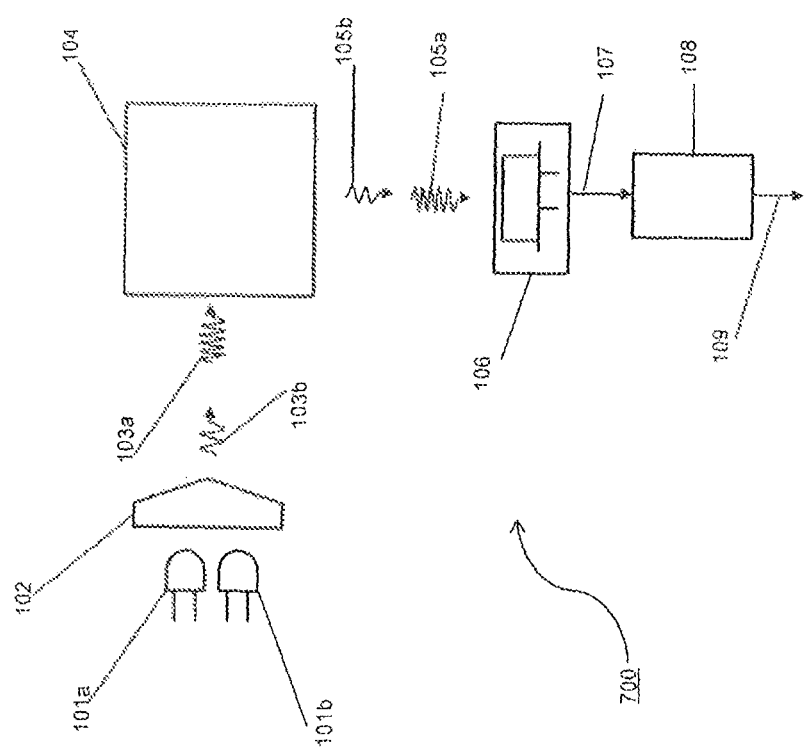

[Fig. 10]
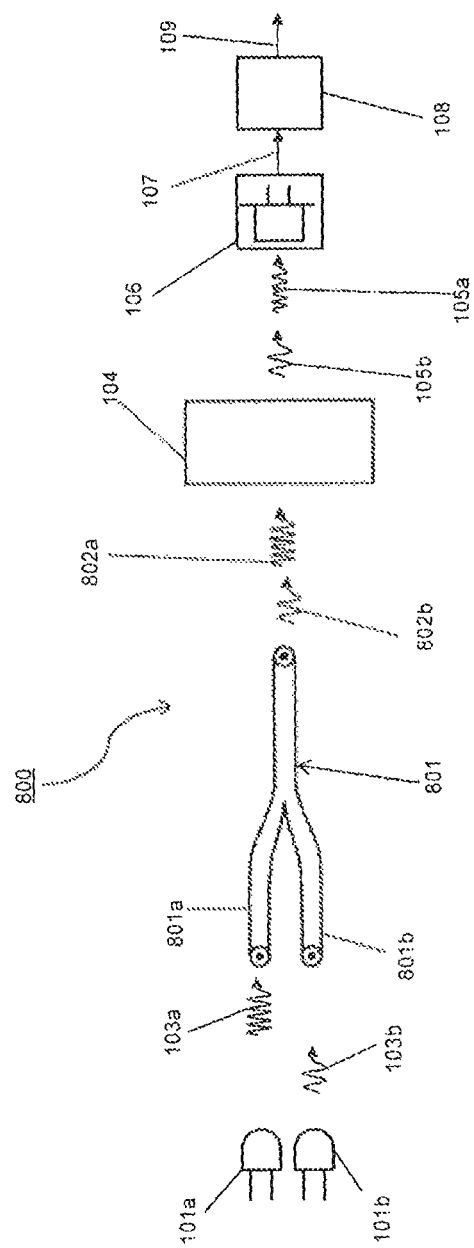

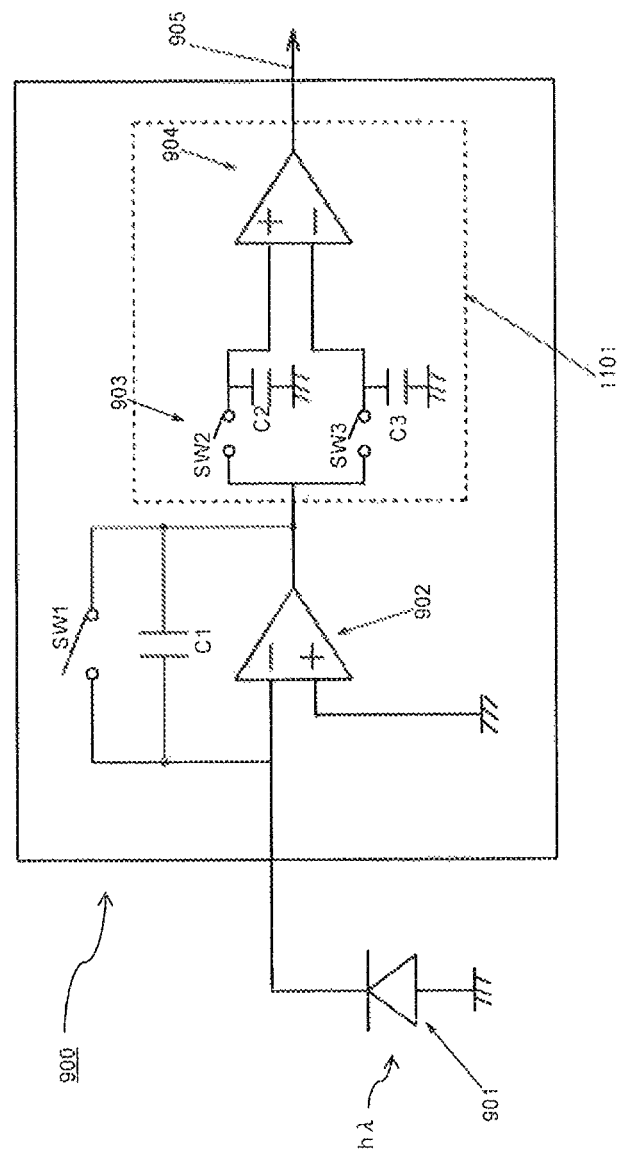
[Fig. 11]

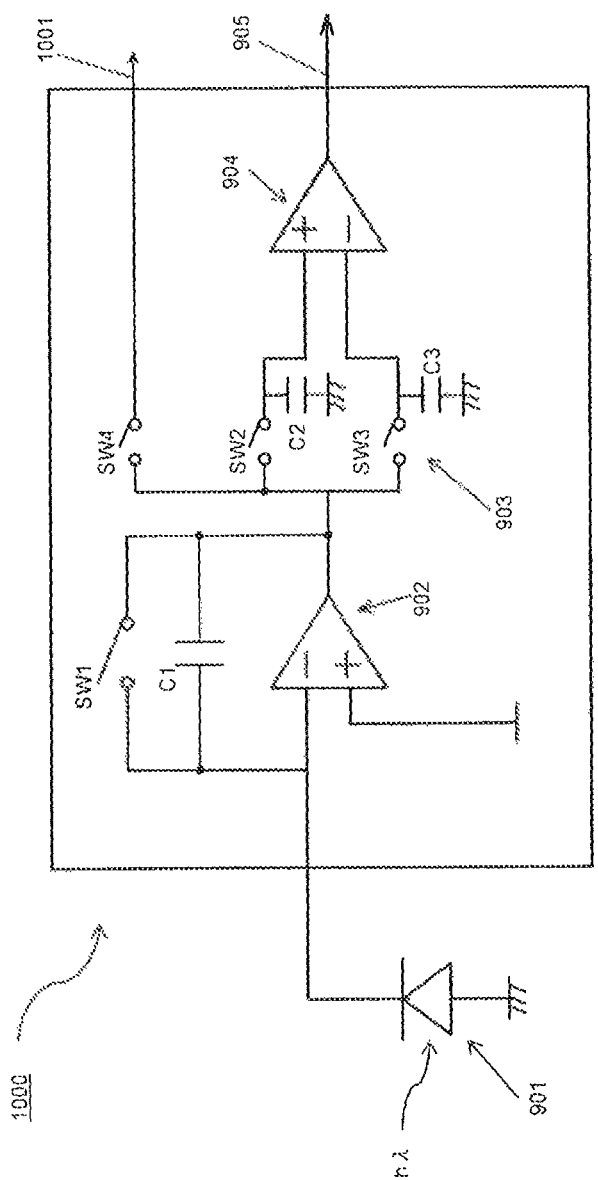
[Fig. 12]

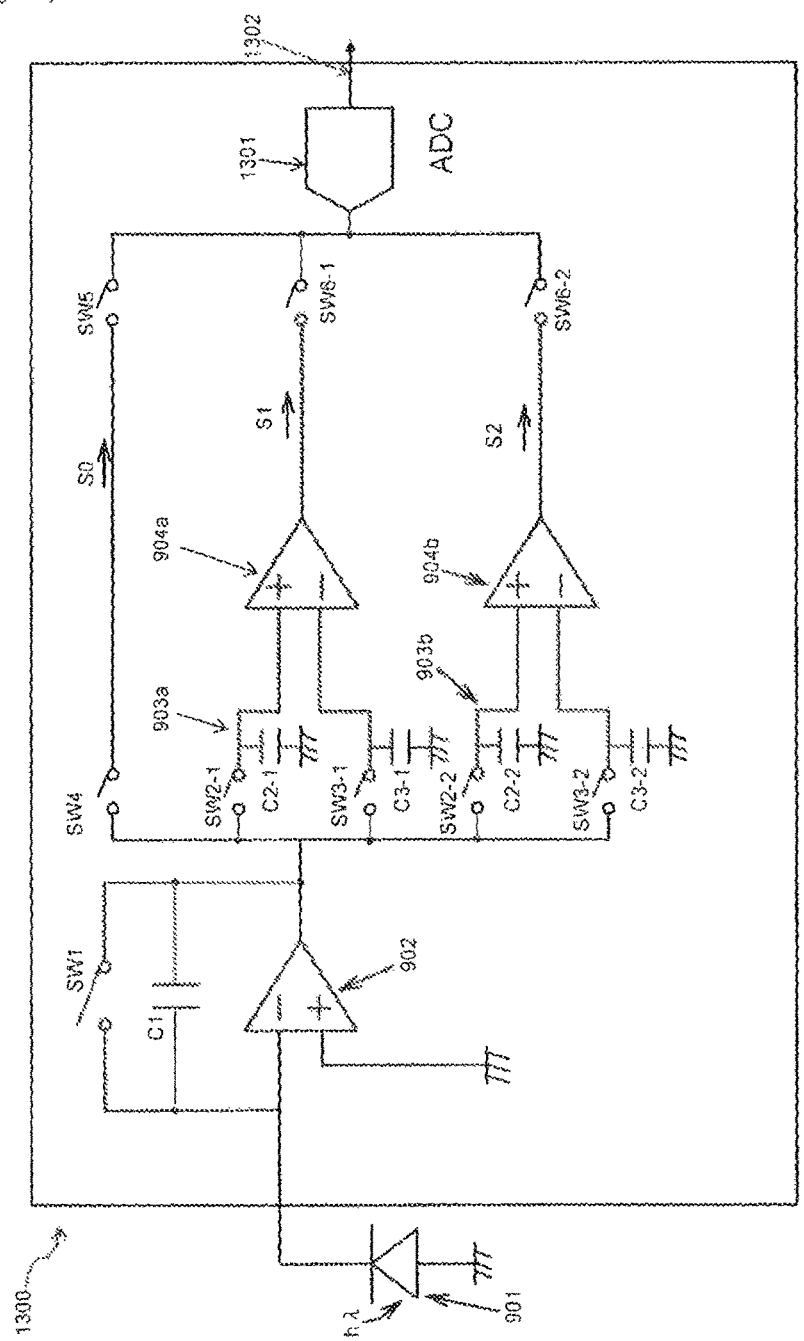
[Fig. 13]

[Fig. 14]
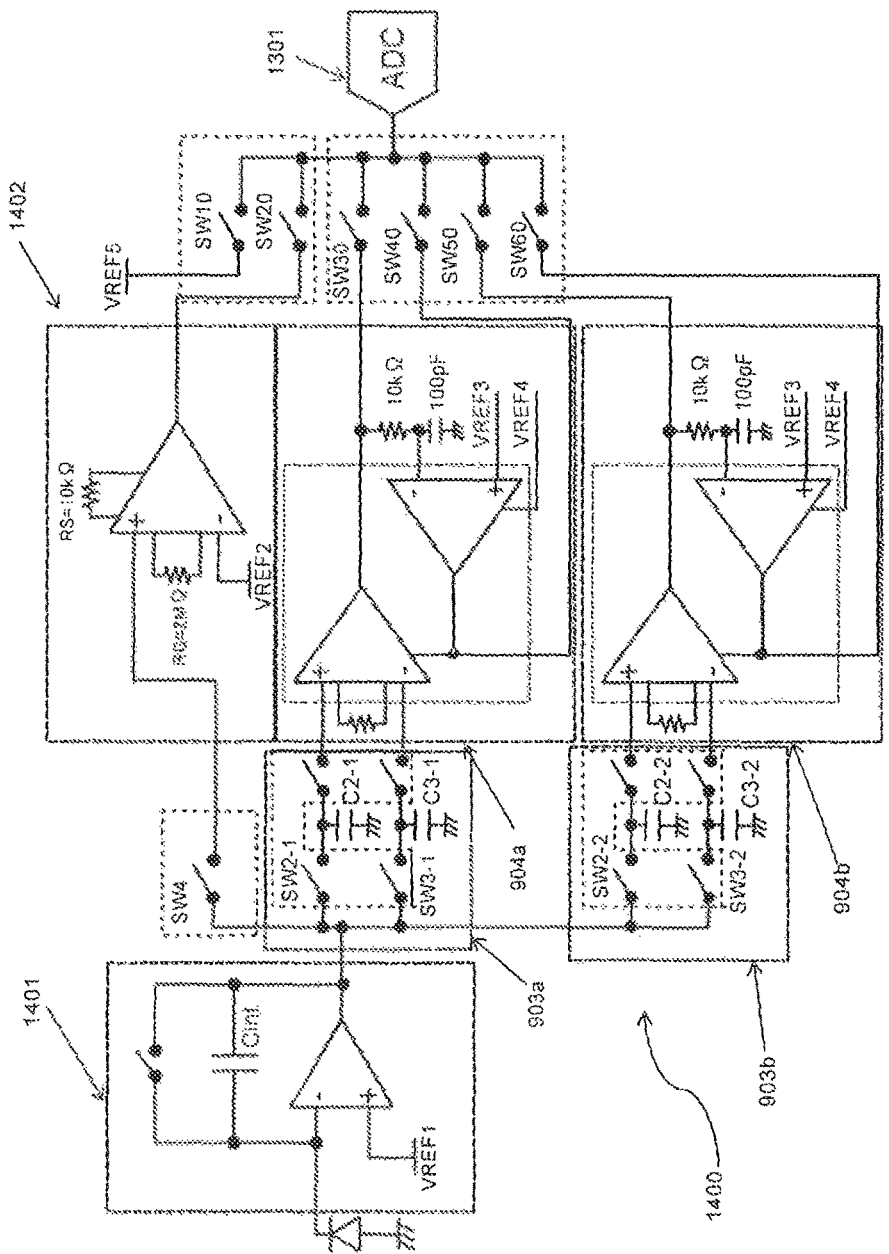

[Fig. 15]
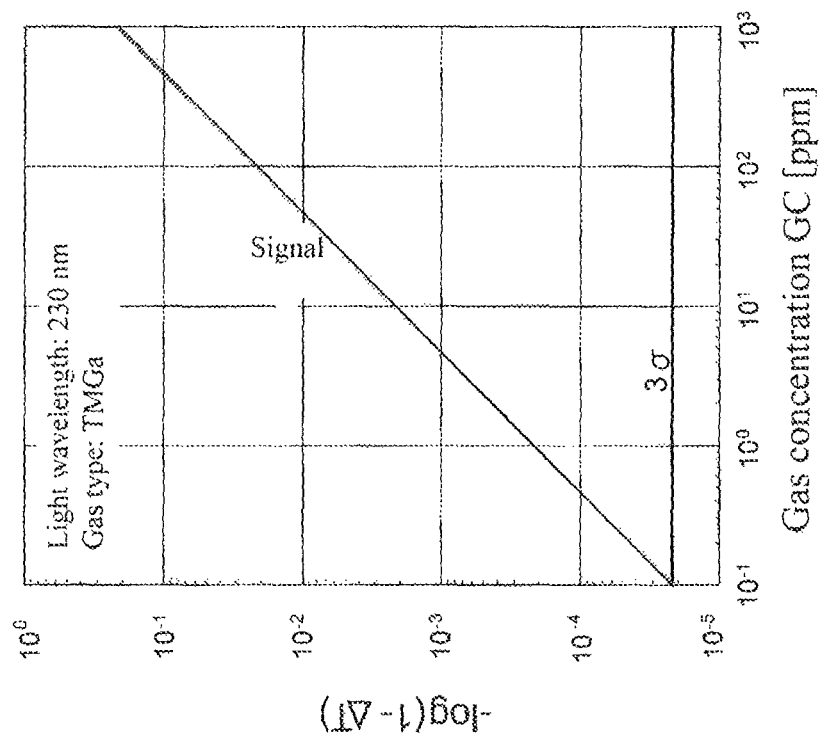

[Fig. 16]
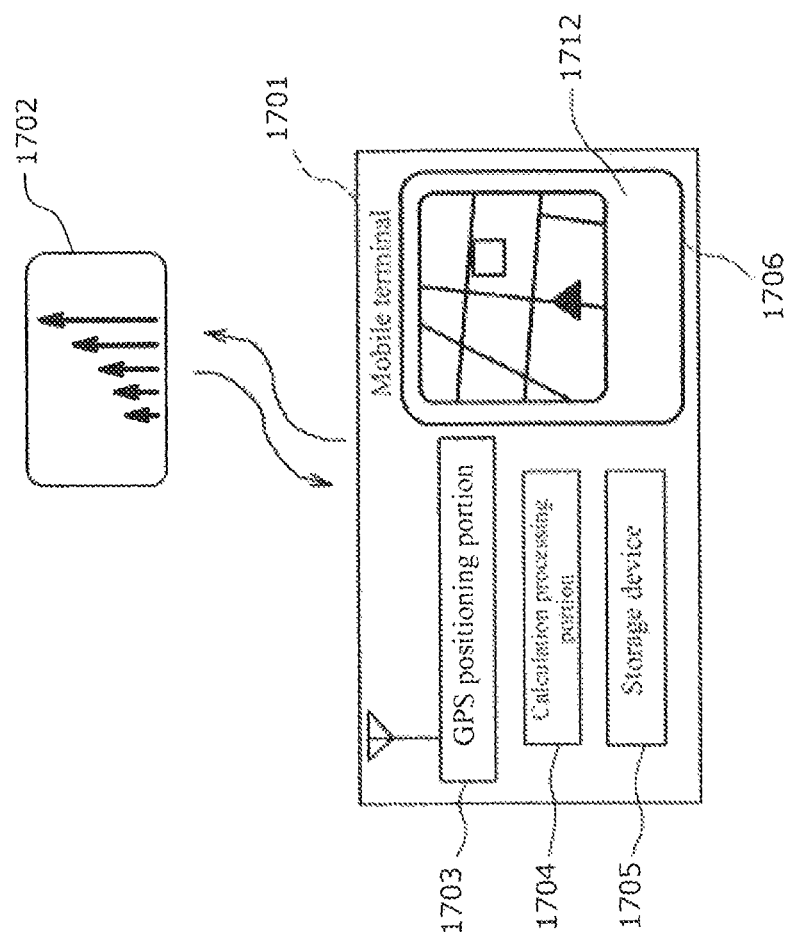

[Fig. 17]
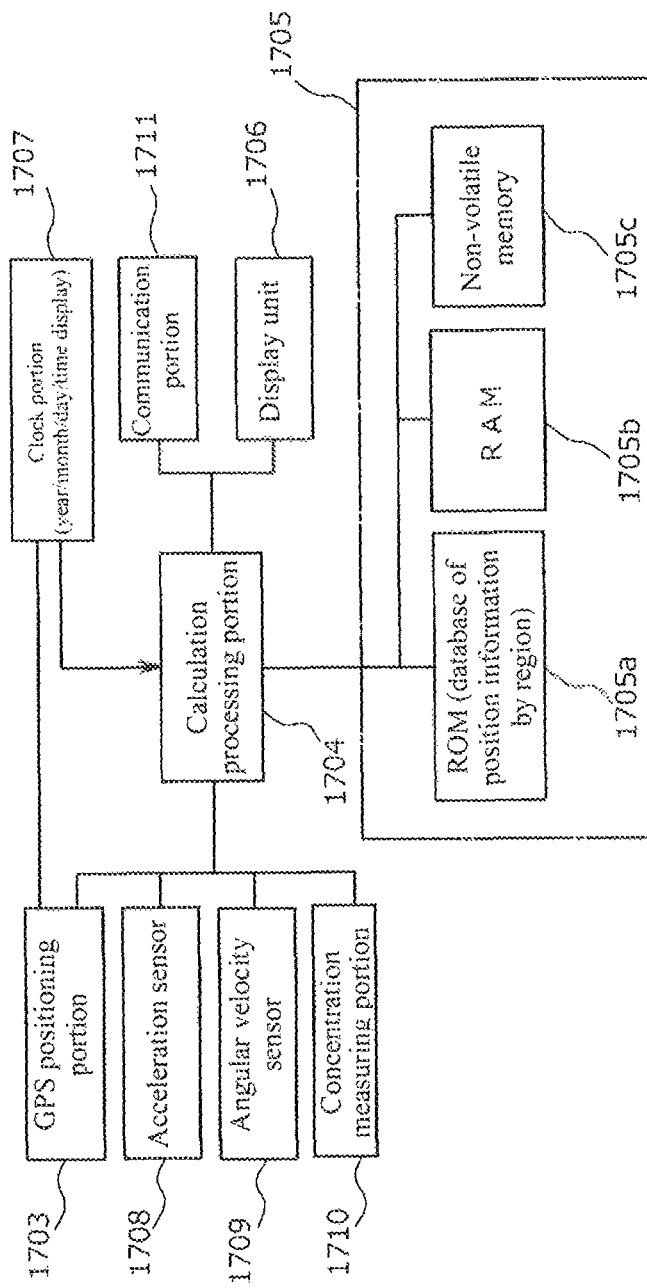

[Fig. 18]
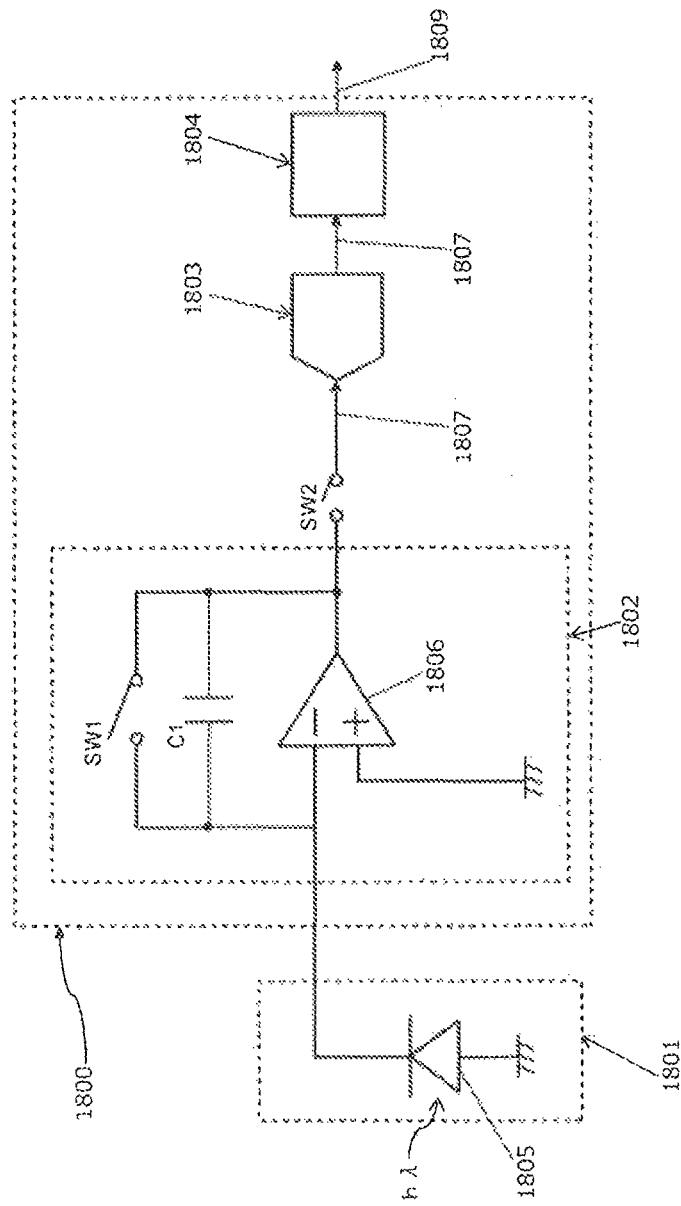

[Fig. 19]
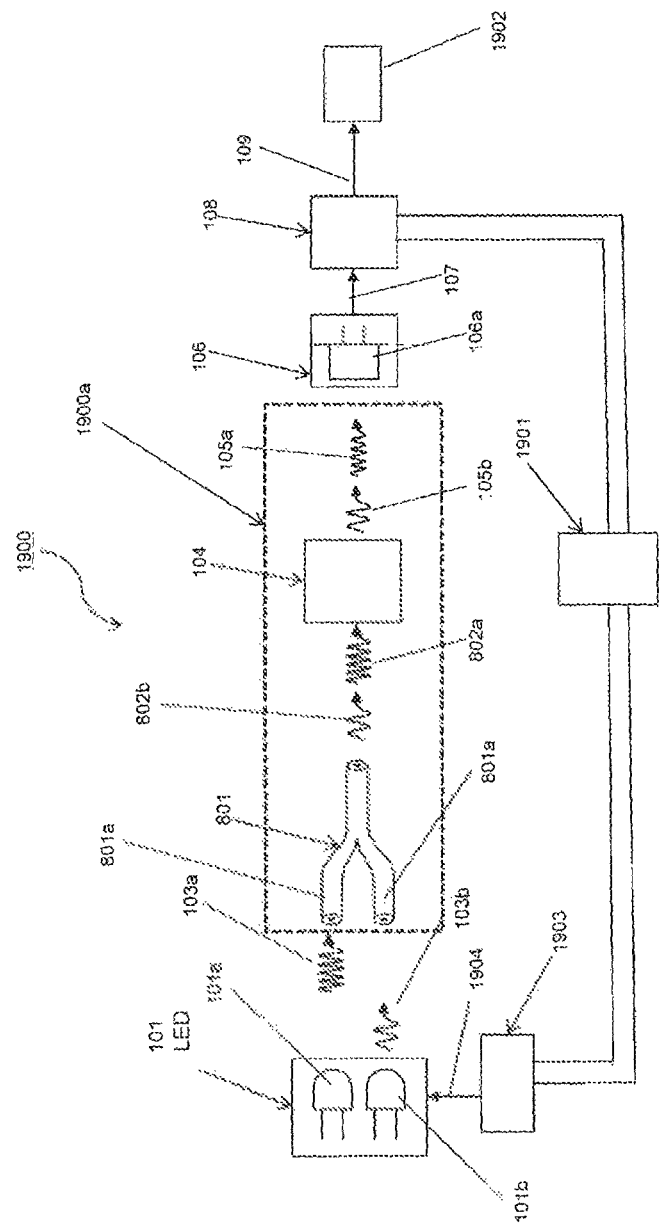

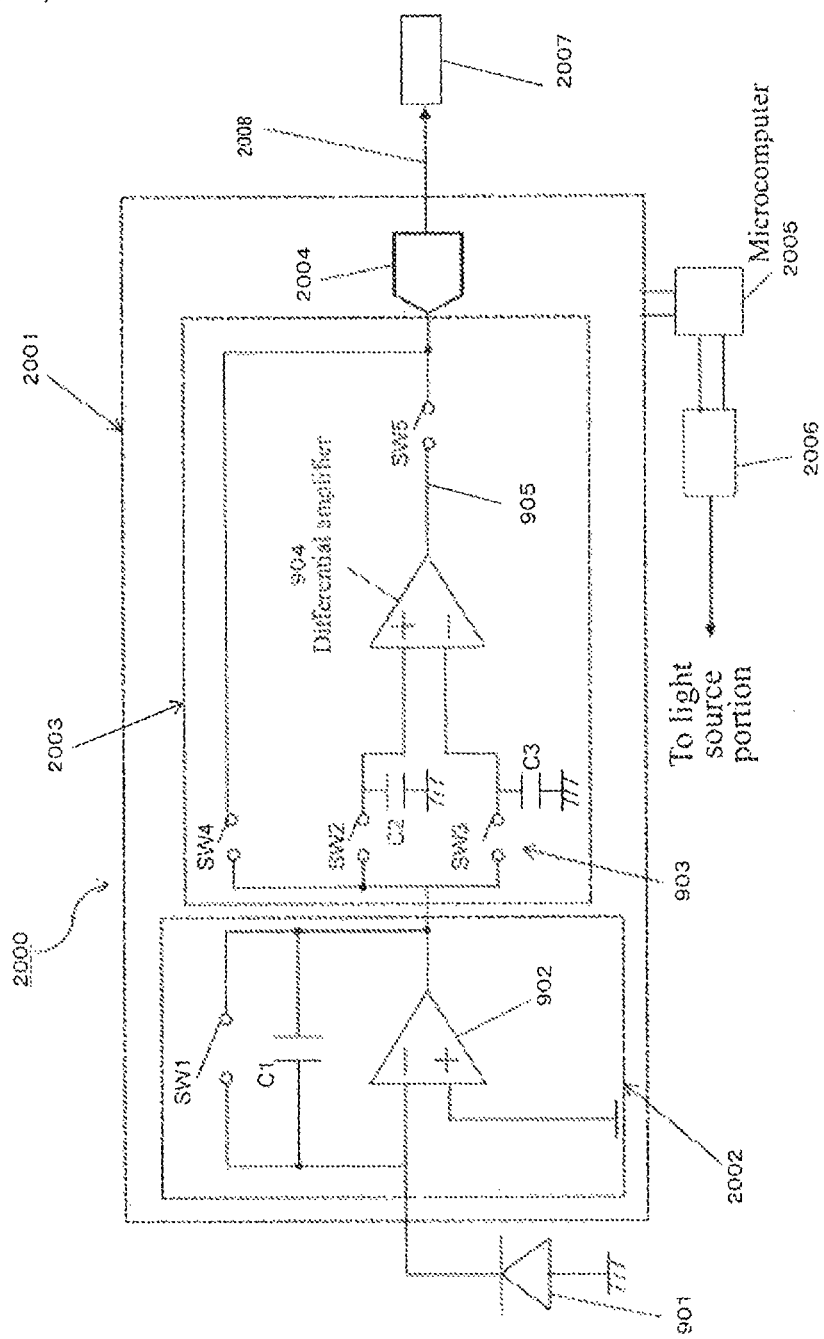
[Fig. 20]

[Fig. 21]
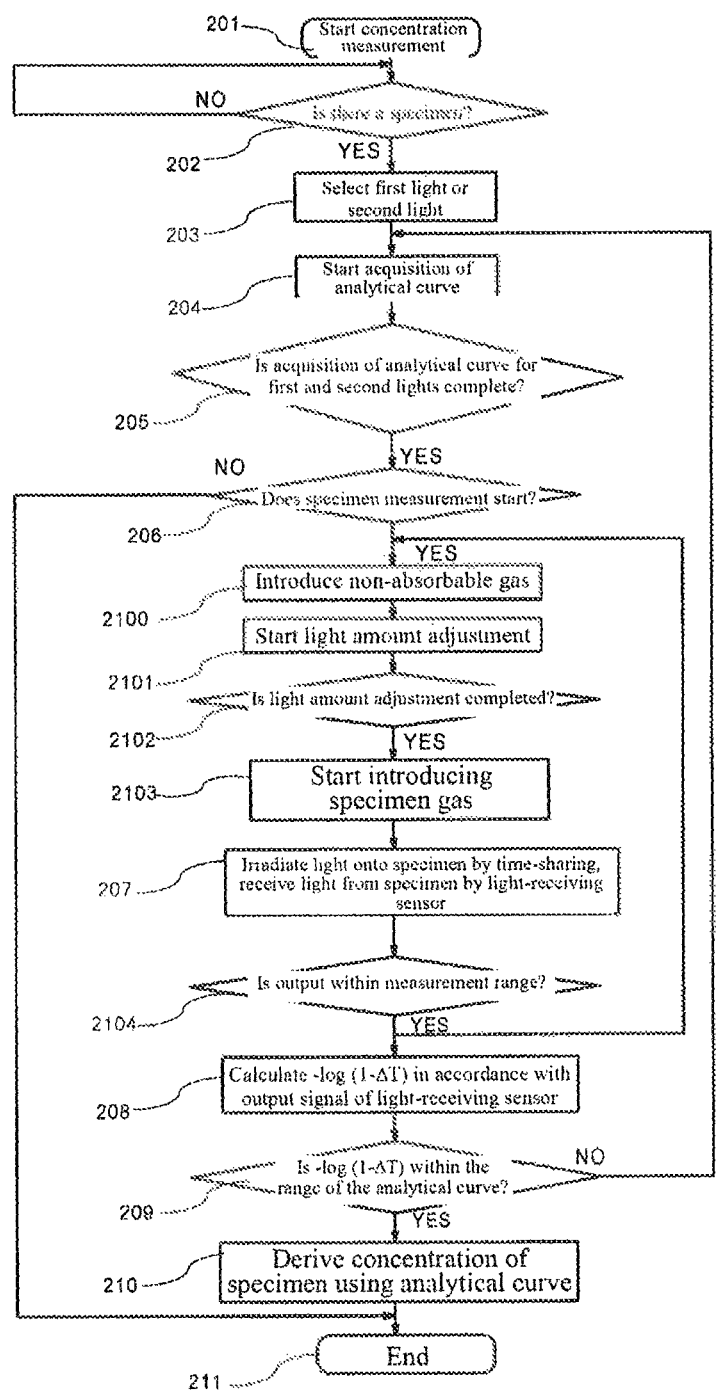

[Fig. 22]

| Step | Adjust light amount | Measure gas concentration | Adjust light amount | Measure gas concentration |
|---|---|---|---|---|
| Introduce gas | Ar or N2 (non-absorbable gas) | Specimen gas | Ar or N2 (non-absorbable gas) | Specimen gas |

→ t

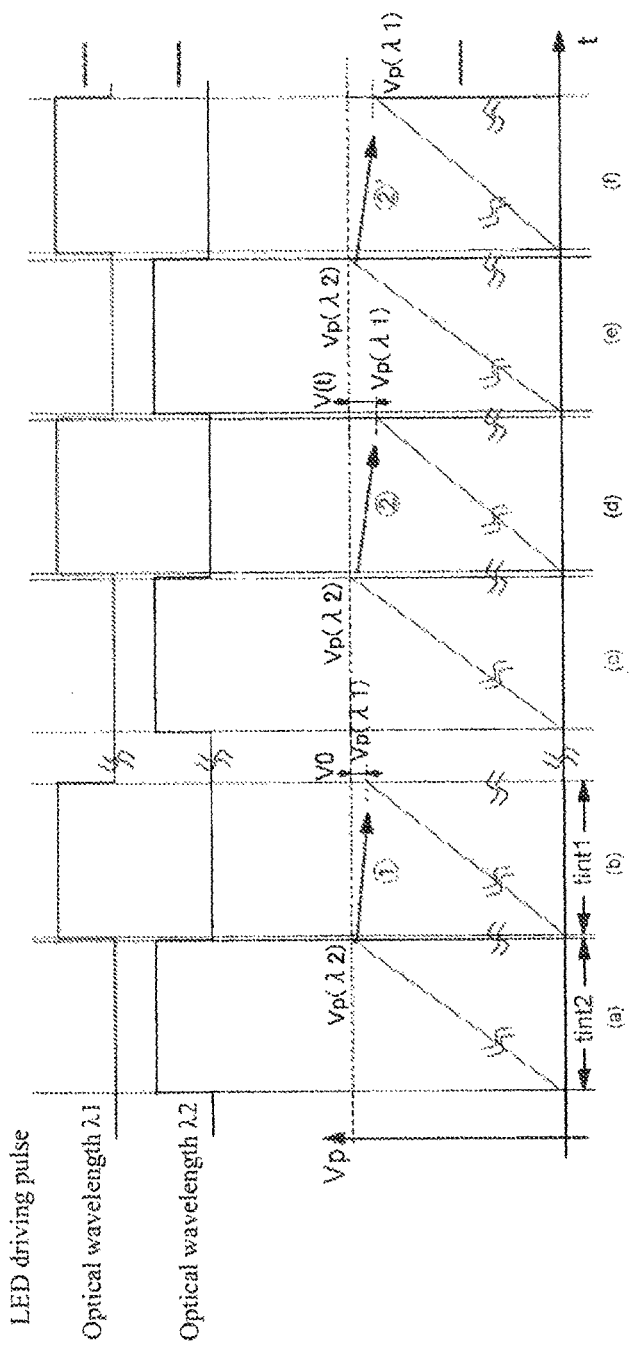
[Fig. 23]

CONCENTRATION MEASURING METHOD

This application is a national phase of PCT Application No. PCT/JP2015/073675 filed Aug. 24, 2015, which in turn claims benefit of Japanese Patent Application No. 2014-176575 filed Aug. 29, 2014 and PCT Application No. PCT/JP2015/055076 filed Feb. 23, 2015.

BACKGROUND OF THE INVENTION

Field of the Invention

The present invention relates to a concentration measuring method related to a concentration of a predetermined chemical component in a liquid or a gas, a sugar content in a fruit or a vegetable, a sake meter value (sweetness/dryness) of Japanese sake, or the like.

Description of the Background Art

In the manufacture of a semiconductor, mixed gases are often supplied from the same line inside a treatment chamber of a semiconductor manufacturing device. The supply of such a mixed gas requires that a mixture ratio of component gases be kept constant during the treatment process period, and instantaneously changed as intended. To this end, a flow rate control device, such as a flow control system component (FCSC), for example, that comprises a gas flow rate measurement mechanism and a gas flow rate adjustment mechanism is arranged in the gas supply line. In this FCSC, the degree to which the flow rate per unit time (hereinafter also referred to as "unit flow rate") of each component gas that constitutes the mixed gas can be accurately measured is important.

Today, in a semiconductor manufacturing process in which there are many opportunities to implement a treatment process such as film formation or etching at an atomic-to nano-order level, the unit flow rate of each component gas in a mixed gas immediately prior to introduction to a treatment chamber needs to be measured accurately and instantaneously down to a range of a small amount.

In such a conventional flow rate control device that satisfies the requirement described above, generally the flow rate of each single component gas prior to mixture is measured and the target mixture ratio of the mixed gas is calculated from the measured flow rate values.

Nevertheless, the mixture ratio of the mixed gas at the moment of introduction into the treatment chamber (hereinafter also referred to as "actual mixture ratio") is not always guaranteed to be the same as the mixture ratio calculated from the measured flow rate values (hereinafter also referred to as "measured mixture ratio") during process execution. Thus, conventionally a feedback mechanism is provided that measures the flow rate of each single component gas either continually or at a predetermined interval, and adjusts each of the flow rates so that, when the flow rate of any single component gases fluctuates, the mixture ratio becomes the original predetermined mixture ratio based on the new value (Patent Document 1, for example).

On the other hand, examples of a gas concentration measuring system include a system that uses a partial pressure measurement sensor that measures the partial pressure of a material gas by a non-dispersive infrared absorption method, and calculates the concentration of the material gas on the basis of the partial pressure measurement value of this sensor by a mathematical operation (Patent Document 2, for example).[0006]

Further, in metal-organic compound chemical vapor deposition (MOCVD; chemical vapor deposition that uses a metal-organic compound) as well, formation of a uniform film requires control of the supplied concentration of the metal-organic compound so that the supplied concentration of the metal-organic compound is constant during the film formation process period, or so that the supplied concentration fluctuates in accordance with the component distribution of the metal-organic compound to ensure formation of a film with a preferred component distribution. Generally, the metal-organic compound is mixed into a carrier gas via bubbling or the like, and supplied to the treatment chamber. The used metal-organic compound is not limited to a single compound, and a plurality of compounds may be used as well. Examples of the method used to supply the raw material gases of a plurality of types of metal-organic compounds in accordance with design values include a method for using infrared gas analysis means (Patent Document 3, for example).

Furthermore, in the field of fruit and vegetable production and shipping as well, measurement of the concentration of a component such as a sweetness component of the fruit or vegetable is important in determining the sales price of the fruit or vegetable to be shipped. That is, the sweetness of a fruit or vegetable such as an apple, pear, peach, persimmon, strawberry, or watermelon significantly affects the sales price of the product, and thus knowing whether or not the sweetness is ideal for harvest for shipping is a matter of keen interest to the fruit and vegetable producer. One method for ascertaining the sweetness of a fruit or vegetable is to measure the sugar content in the fruit or vegetable in a non-contact manner using infrared light (Patent Document 4, for example).

Further, medically related, the ability to instantaneously measure blood components in the bloodstream, for example, such as the red blood cell count, white blood cell count, platelet count, reticulocyte count, and hemoglobin level in a living body in a non-contact (non-destructive, non-invasive) manner without drawing blood would not only alleviate the burden of the patient but also mentally and physically alleviate the labor burden of doctors, nurses, and medical technicians. Thus, the ability to easily and instantaneously take such measurements in a living body in a non-contact, non-invasive manner has been desired. For example, recently the number of diabetes patients in younger demographics is on the rise, increasing the demand for test methods that allow tests to be conducted easily, quickly, and with high accuracy. Furthermore, not only are there many patients under doctor care, but there are many latent patients (potential patients) as well, and the number of cases in which, for example, such a patient experiences a sudden drop in blood sugar level while driving, fully or partially loses consciousness, and causes an accident is increasing daily. While the concentration of glucose (blood sugar level, blood sugar) in the blood is normally continually adjusted within a certain range by the activity of various hormones (insulin, glucagon, cortisol, and the like), when this adjustment mechanism fails for any of a variety of reasons, the amount of sugar in the blood increases abnormally, resulting in diabetes. Diabetes is a disease that refers to a condition in which the blood sugar level (concentration of glucose in the blood) is abnormally high, and is diagnosed when the blood sugar level or hemoglobin A1c value exceeds a certain standard. Diabetes may cause symptoms attributable to the high blood sugar itself and also, over time, glycation in which glucose, having a high concentration in the blood, binds with protein in the vascular endothelium due to the high reactivity of the aldehyde group, resulting in the gradual destruction of microvessels in the body, causing serious disorders (microangiopathies including diabetic neuropathy, diabetic retinopathy, and diabetic nephropathy) in various organs in the body, including the eyes and kidneys (complications). Thus, appropriate blood sugar management is important in the treatment of diabetes, including continual strict blood sugar control, medical diet and therapeutic exercise review, insulin dose adjustment and review, verification/prediction of low blood sugar by medical treatment, alleviation of low blood sugar anxiety, and avoidance of severe hyperglycemia.

Measurement of blood sugar level in medical institutions such as hospitals is generally performed by a so-called invasive method for drawing blood from a finger, arm, or the like of the living body. Further, diabetes patients are tested for blood sugar level during treatment under the care of a physician in the hospital. On the other hand, in many cases the blood sugar level needs to be measured daily, and thus a patient must often perform blood sugar level measurements on his or her own using a self-monitoring of blood glucose (SMBG) device in a hospital bed or at home. While measurement has become rather simple, blood still must be drawn either by the patient or with the help of another. Blood is drawn by puncturing a finger or an arm. This puncturing is associated with pain and a puncture wound, placing physical and mental stress on the patient. While recently the use of a painless needle may be considered, association with a puncture wound cannot be avoided, and health safeguards for preventing infection caused by open wounds and the like are required. Recently, as a solution to this problem, non-invasive methods are proposed (Patent Documents 5 and 6, for example).

On the other hand, in Japan, both the blood sugar level and the hemoglobin A1c value must be measured to assess diabetes. Examples of methods for measuring both the blood sugar level and the hemoglobin A1c value include the method set forth in Patent Document 7.

Furthermore, a method that allows measurement of a sake meter value (hereinafter "SMV"), acidity, and amino acidity in the manufacturing process of Japanese sake, with high accuracy, promptness, and a simple configuration, has been in demand. Japanese sake is a liquor delicate in flavor and aroma. Japanese sake is gauged in terms of sweetness/dryness by its SMV, and in terms of full-bodied/light flavor by its acidity. The SMV refers to the amount of sugar and acid dissolved in the sake, and is a unit that expresses the specific gravity of the refined sake. The SMV is measured by bringing the temperature of the sake to be measured to 15° C., and then floating a hydrometer called an SMV meter in the sake. Japanese sake having the same weight as distilled water at 4° C. is given an SMV of "0." Any lighter sake is indicated by a positive (+) value, and any heavier sake is indicated by a negative (−) value. In Japanese sake, what determines sweetness is glucose concentration.

In contrast to SMV which gauges sweetness/dryness, acidity (level of light/full-bodied flavor) gauges richness and depth. A Japanese sake with a higher acidity has a more full-bodied flavor, while a Japanese sake with a lower acidity has a lighter flavor. Given the same SMV, a Japanese sake with a high acidity is spicier while a sake with a low acidity is sweeter. Conversely, a Japanese sake with low acidity tends to lack a smooth, clean finish, and have a shallow flavor. This acidity, however, affects not only richness, but the actual sweet/spicy flavor as well. In general, a higher acidity tends to result in a spicier taste. Conversely, a low acidity results in a sweeter taste, even if the sugar content is not high. Acidity is measured by the number of titration millimeters of a 1/10 normal sodium hydroxide solution that is required to neutralize 10 milliliters of the refined sake. If this value is high, expressions such as "plain" are used. If this value is low, expressions such as "rich" are used. Further, with Japanese sake, amino acidity (tastiness) is also important. Amino acids are elements that bring savoriness, and high amino acidity results in an increase in savory elements, and thus a rich sake flavor. However, savoriness does not necessarily increase as the amino acidity is increased, resulting in an off-flavor when too high.

As described above, in the manufacture of Japanese sake, the management of SMV, acidity, and amino acidity significantly affects the business value (hereinafter also referred to as "sales value") of the manufactured sake. The SMV, acidity, and amino acidity sensitively fluctuate according to humidity, temperature, and sanitary aspects, and thus humidity, temperature, and sanitary aspects are strictly controlled in the manufacture of Japanese sake and SMV, acidity, and amino acidity are frequently measured in the manufacturing process.

PATENT DOCUMENTS

Patent Document 1: Japanese Laid-Open Patent Application No. 2012-138407
Patent Document 2: Japanese Laid-Open Patent Application No. 2010-109304
Patent Document 3: Japanese Laid-Open Patent Application No. 2006-324532
Patent Document 4: Japanese Laid-Open Patent Application No. 2003-114191
Patent Document 5: Japanese Laid-Open Patent Application No. 2008-256398
Patent Document 6: Japanese Laid-Open Patent Application No. 2006-141712
Patent Document 7: Japanese Laid-Open Patent Application No. 2012-137500

SUMMARY OF THE INVENTION

Problems to be Solved by the Invention

In the concentration measuring method or concentration adjustment method set forth in each of the patent documents described above, problems such as the following exist.

In Patent Document 1, the flow rate is measured on an upstream side of the treatment chamber and merely fed back, and thus the problem of whether or not the measured mixture ratio and actual mixture ratio are identical remains unresolved. Furthermore, while the length of the supply line from the mixing position to the position of introduction into the treatment chamber needs to be adequately set to ensure that the mixed state of the gases is uniform, doing so makes it all the more difficult to regard the measured mixture ratio and actual mixture ratio as identical. To ensure that the measured mixture ratio and the actual mixture ratio are identical, one may consider positioning the mixing position and the introduction position as close to each other as possible, but doing so results in the problem that it is difficult to guarantee a uniform mixture. Attempting to resolve such problems in addition to the problems described above results in an increasingly complex mechanism, and requires rather advanced control technology. Additionally, according to the configuration of Patent Document 1, measurement is performed by flow rate measurement, and thus gases cannot be specified.

In the case of Patent Document 2, measurement is performed by partial pressure measurement and thus the method is unsuitable for such high accuracy measurement as addressed here. Furthermore, the measurement error undeniably increases when the partial pressure measurement is performed in a range of an extremely small order.

The method disclosed in Patent Document 3 is configured to individually adjust any one of first infrared gas analysis means for measuring the concentration of each raw material gas in a mixed gas supplied from a gas mixing chamber to a reaction chamber, second infrared gas analysis means for measuring a concentration of each raw material gas in a discharged gas discharged from the reaction chamber, the flow rate control means for calculating an amount of consumption of each raw material gas inside the reaction chamber based on the measurement results of the first and second infrared gas analysis means and setting the difference between the calculated value and a predetermined design value as a control amount, a gas supply source temperature control unit, and a substrate temperature control unit. Thus, the raw material gases consumed not by film formation but by an inner wall surface of the reaction chamber and the like are not taken into consideration, making it difficult to form a thin film having a uniform film thickness and uniform components. Moreover, a specific example of the infrared gas analysis means is not illustrated in Patent Document 3. As a result, while formation of a thin film having uniform components and a uniform film thickness at the nano-order level requires strict control of the supplied concentration of the metal-organic compound in order to supply the metal-organic compound to the treatment chamber at a predetermined concentration for a certain period of time, demanding high accuracy in concentration measurement, this demand is not simply satisfied.

The method set forth in Patent Document 4 irradiates two monochromatic lights having different wavelengths onto a fruit or a vegetable, determines each coefficient of an identification formula from values of light transmittances Ta, Tb of a plurality of actual measurement examples in relation to each monochromatic light and values of a sugar content C of actual measurements of the examples, and uses the data of each determined coefficient as well as the measured light transmittances of the two monochromatic lights to find the sugar content using the identification formula. This method, therefore, merely finds the average sugar content of the fruit or vegetable subjected to sugar content measurement. Thus, in the case of a fruit or a vegetable having a high sugar content near the peel or core, it may be difficult to avoid inclusion of a fruit or a vegetable that has an inadequate sugar content depending on the section consumed and thus decreases product price in a shipment.

In the methods of Patent Documents 5 and 6, measurement errors attributable to patient nervousness and perspiration in the affected measurement region or a rise in body temperature cannot be avoided. Measurement methods of a blood sugar measuring device include enzyme electrode methods and enzyme colorimetric (colorimetric determination) methods. Enzyme electrode methods include glucose oxidase (GOD) methods and glucose dehydrogenase (GDH) methods. Enzyme colorimetric (colorimetric determination) methods include hexokinase (HX) methods and glucose oxidase/peroxidase (GOD/POD) methods. However, while errors are not evident in the measurement value of each device, when a hematocrit (a test for checking the percentage of red blood cells in a given sample of blood) value is between 20% and approximately 60%, the problem arises that the methods indicate a high value for blood having a hematocrit value below 20%, such as in patients with severe anemia or dialysis patients, and conversely a low value for hypervolemic blood having a hematocrit value above 55%, such as in newborns and in women prior to menstruation. Thus, the methods are inappropriate for patients with severe anemia and dialysis patients. Furthermore, GOD methods are problematic in that the measured blood sugar level decreases to the extent that the partial pressure of the dissolved oxygen in the blood is high. Thus, GOD methods are not appropriate for patients that use oxygen for breathing control. In addition, a normal measurement value may not be obtained for reasons attributable to verification of blood drawing and blood dotting procedures, how the test paper is attached, how the measurement device is used, and the like.

The method set forth in Patent Document 7 takes measurements using the same measurement principle of detecting coloring from hemoglobin, coloring from saccharized hemoglobin, and coloring from glucose by reflecting light having different wavelengths. While offering the advantages of simplifying and reducing the size of the device, the method requires a reagent and coloring work for three types of coloring, i.e., hemoglobin, saccharized hemoglobin, and glucose, and also comes with the burden of drawing blood.

Further, while humidity, temperature, and sanitary aspects are strictly controlled in the manufacture of Japanese sake, and SMV, acidity, and amino acidity are frequently measured in the manufacturing process, a method for measuring SMV, acidity, and amino acidity quickly and accurately down to a concentration range of an extremely small amount in a non-destructive manner using simple means has not yet been provided.

As understood from the above description, a concentration measuring method that allows quick and accurate measurement of a concentration of a predetermined chemical component down to a concentration range of an extremely small amount in a non-destructive manner using simple means has not yet been provided.

Further, a concentration measuring method that allows measurement of the concentrations of a plurality of chemical components in an object to be measured with high accuracy in real time using the same measurement system and the same conditions, regardless if the component is a gas, a liquid, or a solid, has not yet been provided.

Furthermore, a concentration measuring method that allows quick and accurate measurement of the concentration of a chemical component in an object to be measured down to a concentration range of an extremely small amount in the nano order in real time, the method having universality, i.e., the ability to be embodied in various forms and modes, has not yet been provided.

Furthermore, a concentration measuring method that allows quick and accurate measurement of the concentrations of a plurality of chemical components in an object to be measured in real time using a simple configuration has not yet been provided.

The present invention was achieved as a result of close research on the points described above.

It is therefore an object of the present invention to provide a concentration measuring method that allows quick and accurate measurement of a concentration of a chemical component in real time, using a simple configuration.

Another object of the present invention is to provide a concentration measuring method that allows quick and accurate measurement of a concentration of a chemical component in an object to be measured, down to a concentration range of an extremely small amount in the nano order in real time using a simple configuration, regardless if the component is a gas, a liquid, or a solid, the method having universality, i.e., the ability to be embodied in various forms and modes.

Yet another object of the present invention is to provide a concentration measuring method that allows quick and accurate measurement of a concentration of a chemical component in a non-destructive, non-contact manner, down to a range of an extremely small amount using a simple configuration.

Yet another object of the present invention is to provide a concentration measuring method that allows measurement of a concentration of a chemical component, down to a range of an extremely small amount with measurement errors based on environmental fluctuations and characteristic fluctuations in system components, such as electrical circuits or electronic elements, eliminated at least to the extent substantially possible.

Yet another object of the present invention is to provide a concentration measuring method that allows measurement of a blood sugar level in a non-invasive manner using a simple configuration and method in a state that is at least substantially free of measurement errors attributable to patient nervousness and perspiration in the affected measurement region or a rise in body temperature (errors based on the physiological state of a specimen or an object to be measured; hereinafter also referred to as "physiological errors").

Yet another object of the present invention is to provide a concentration measuring method that allows quick and accurate measurement of concentrations of a plurality of chemical components in an object to be measured in real time, using a simple configuration.

Yet another object of the present invention is to provide a concentration measuring method that allows simple and easy measurement of both a blood sugar level and a hemoglobin A1c value using the same configuration and method.

Means for Solving the Problems

A first aspect of the present invention is a concentration measuring method for optically measuring a concentration of a predetermined chemical component in an object to be measured, the method comprising the steps of:
irradiating at least light (1) having a first wavelength ($\lambda 1$) that has an absorbability with respect to the chemical component, and light (2) having a second wavelength ($\lambda 2$) that has no or substantially no absorbability with respect to the chemical component, or an absorbability that is relatively lower than that of the light having the first wavelength, from light-emitting means toward the object to be measured using a time-sharing method;
sequentially receiving the light that is produced by the irradiation and passes through the object to be measured by light-receiving means;
inputting a first light-receiving signal (1) based on the light (1) and a second light-receiving signal (2) based on the light (2), each produced by the received light into differential signal forming means; deriving the concentration of the predetermined chemical component from a measured value based on a differential signal output from the differential signal forming means in accordance with the input, and data stored in storage means in advance; and
feeding back a feedback signal corresponding to the differential signal to light emission amount control means for controlling a light emission amount of the light-emitting means and/or the differential signal forming means.

A second aspect of the present invention is a concentration measuring method for optically measuring a concentration of a predetermined chemical component in an object to be measured, the method comprising the steps of:
irradiating at least light having a first wavelength that has an absorbability with respect to the chemical component, and light having a second wavelength that has no or substantially no absorbability with respect to the chemical component, or an absorbability that is relatively lower than that of the light having the first wavelength, from a single light-emitting means toward the object to be measured using a time-sharing method;
sequentially receiving the light that is produced by the irradiation and passes through the object to be measured in a time-sharing manner by a single light-receiving means;
inputting a first light-receiving signal based on the light having the first wavelength and a second light-receiving signal based on the light having the second wavelength, each produced by the received light, into differential signal forming means;
deriving the concentration of the predetermined chemical component from a measured value based on an output signal output from the differential signal forming means in accordance with the input, and data stored in storage means in advance; and
controlling a light emission amount of the light-emitting means on the basis of a feedback signal corresponding to the differential signal.

A third aspect of the present invention is a concentration measuring method comprising the steps of: irradiating at least light having a first wavelength and light having a second wavelength, each having a different light absorptivity with respect to an object to be measured, onto the object to be measured using a time-sharing method;
sequentially receiving the light of each wavelength that optically passes through the object to be measured as a result of the irradiation of the light of each wavelength, using a common light-receiving sensor;
forming a differential signal between a signal related to the light having the first wavelength and a signal related to the light having the second wavelength output from the light-receiving sensor in accordance with the received light;
deriving a concentration of a chemical component in the object to be measured on the basis of the differential signal; and
controlling the amount of light during the emission of at least one of the light having the first wavelength and the light having the second wavelength on the basis of a feedback signal corresponding to the differential signal.

A fourth aspect of the present invention is a concentration measuring method comprising the steps of: irradiating a first light and a second light, each having a different light absorptivity with respect to an object to be measured, onto the object to be measured using a time-sharing method;
receiving each light that optically passes through the object to be measured by irradiation of each light onto the object to be measured, using a common light-receiving sensor;
forming a differential signal on the basis of a signal related to the first light and a signal related to the second light output from the light-receiving sensor in accordance with the received light; deriving a concentration of a predetermined chemical component in the object to be measured on the basis of the differential signal; and
controlling the amount of light during the emission of at least one of the light having the first wavelength and the light having the second wavelength on the basis of a feedback signal corresponding to the differential signal.

A fifth aspect of the present invention is a concentration measuring method comprising the steps of: irradiating at least light having a first wavelength and light having a second wavelength, each having a different light absorptivity with respect to an object to be measured, onto the object to be measured using a time-sharing method;

receiving the light of each wavelength that optically passes through the object to be measured as a result of the irradiation of the light of each wavelength, using a common light-receiving sensor;

forming a differential signal between a signal related to the light having the first wavelength and a signal related to the light having the second wavelength output from the light-receiving sensor in accordance with the received light;

deriving a concentration of a chemical component in the object to be measured on the basis of the differential signal; and controlling the amount of light during the emission of at least one of the light having the first wavelength and the light having the second wavelength on the basis of a feedback signal corresponding to the differential signal.

A sixth aspect of the present invention is a concentration measuring method comprising the steps of: irradiating at least a first light and a second light, each having a different light absorptivity with respect to an object to be measured, onto the object to be measured using a time-sharing method; receiving each light that optically passes through the object to be measured by irradiation of each light onto the object to be measured, using a common light-receiving sensor; forming a differential signal on the basis of a signal related to the first light and a signal related to the second light output from the light-receiving sensor in accordance with the received light; deriving a concentration of a predetermined chemical component in the object to be measured on the basis of the differential signal; and controlling the amount of light during the emission of at least one of the light having the first wavelength and the light having the second wavelength on the basis of a feedback signal corresponding to the differential signal.

A seventh aspect of the present invention is a concentration measuring method for optically measuring a concentration of a predetermined chemical component in an object to be measured, the method comprising the steps of irradiating at least light having a first wavelength that has an absorbability with respect to the chemical component, and light having a second wavelength that has no or substantially no absorbability with respect to the chemical component or an absorbability that is relatively lower than that of the light having the first wavelength from a single light-emitting means toward the object to be measured using a time-sharing method, receiving the light produced by the irradiation from the object to be measured by a single light-receiving means, inputting a first light-receiving signal based on the light having the first wavelength and a second light-receiving signal based on the light having the second wavelength, each produced by the received light, into a differential circuit, comparing a measured value based on an output signal output from the differential circuit in accordance with the input with data stored in advance in storage means, and deriving the concentration of the predetermined chemical component accordingly.

An eighth aspect of the present invention is a concentration measuring method comprising the steps of irradiating at least light having a first wavelength and light having a second wavelength, each having a different light absorptivity with respect to an object to be measured, onto the object to be measured using a time-sharing method, receiving the light of each wavelength that optically passes through the object to be measured as a result of the irradiation of the light of each wavelength using a common light-receiving sensor, forming a differential signal between a signal related to the light having the first wavelength and a signal related to the light having the second wavelength output from the light-receiving sensor in accordance with the received light; and deriving a concentration of a chemical component in the object to be measured on the basis of the differential signal.

A ninth aspect of the present invention is a concentration measuring method comprising the steps of irradiating at least a first light and a second light, each having a different light absorptivity with respect to an object to be measured, onto the object to be measured using a time-sharing method, receiving each light that optically passes through the object to be measured by irradiation of each light onto the object to be measured using a common light-receiving sensor, forming a differential signal on the basis of a signal related to the first light and a signal related to the second light output from the light-receiving sensor in accordance with the received light, and deriving a concentration of a predetermined chemical component in the object to be measured on the basis of the differential signal.

Effect of the Invention

According to the present invention, it is possible to measure a concentration of a predetermined chemical component quickly and accurately in a non-destructive manner down to a concentration range of an extremely small amount using simple means.

Further, it is possible to measure with high accuracy the concentrations of a plurality of chemical components in an object to be measured in real time using the same measurement system and the same conditions, regardless if the component is a gas, a liquid, or a solid.

Furthermore, it is possible to provide a concentration measuring method that allows quick and accurate measurement of a concentration of a chemical component in an object to be measured, down to a concentration range of an extremely small amount in the nano order in real time, the method having universality, i.e., the ability to be embodied in various forms and modes.

BRIEF DESCRIPTION OF THE DRAWINGS

FIG. 1 is a timing chart for explaining the principles of a concentration measuring method of the present invention.

FIG. 2 is a block diagram for explaining a configuration of a preferred embodiment of an optical concentration measuring system that embodies the concentration measuring method of the present invention.

FIG. 3 is a flowchart for explaining a preferred embodiment of the concentration measuring method of the present invention.

FIG. 4 is a timing chart for explaining a signal output timing of the example in FIG. 3.

FIG. 5 is a flowchart for finding an analytical curve.

FIG. 6 is a graph of a relationship between a gas concentration GC and "$-\log(1-\Delta T)$."

FIG. 7 is an explanatory schematic configuration view for explaining main components of a preferred embodiment of the optical concentration measuring system that embodies the concentration measuring method of the present invention.

FIG. 8 is an explanatory schematic configuration view for explaining main components of another preferred embodiment of the optical concentration measuring system that embodies the concentration measuring method of the present invention.

FIG. 9 is an explanatory schematic configuration view for explaining main components of yet another preferred embodiment of the optical concentration measuring system that embodies the concentration measuring method of the present invention.

FIG. 10 is an explanatory schematic configuration view for explaining main components of yet another preferred embodiment of the optical concentration measuring system that embodies the concentration measuring method of the present invention.

FIG. 11 is an explanatory schematic configuration view for explaining a preferred example of a differential signal forming portion adopted in the present invention.

FIG. 12 is an explanatory schematic configuration view for explaining another preferred example of the differential signal forming portion adopted in the present invention.

FIG. 13 is an explanatory schematic configuration view for explaining yet another preferred example of the differential signal forming portion adopted in the present invention.

FIG. 14 is an explanatory schematic configuration view for explaining yet another preferred example of the differential signal forming portion adopted in the present invention.

FIG. 15 is a graph showing a relationship between an absorbance value measured with respect to a gas concentration and a value equivalent to three times a standard deviation of a noise superimposed on the measured signal.

FIG. 16 is an outline external view illustrating an embodiment of a case in which the present invention is applied to a mobile terminal device.

FIG. 17 is a block diagram of an internal configuration of an embodiment in a case in which the present invention is applied to a mobile terminal device.

FIG. 18 is an explanatory schematic configuration view for explaining yet another preferred example of the differential signal forming portion adopted in the present invention.

FIG. 19 is an explanatory schematic configuration view for explaining main components of yet another preferred embodiment of the optical concentration measuring system that embodies the concentration measuring method of the present invention.

FIG. 20 is an explanatory schematic configuration view for explaining main components of yet another preferred embodiment of the optical concentration measuring system that embodies the concentration measuring method of the present invention.

FIG. 21 is a flowchart for explaining a preferred embodiment of the concentration measuring method of the present invention.

FIG. 22 is a diagram illustrating the timing of a gas concentration measuring step, light amount adjustment, and gas introduction illustrated in the flowchart in FIG. 21.

FIG. 23 is a timing chart of an ON/OFF state of light emission of each light source, and an output Vp of an integrating amplifier illustrated in the flowchart in FIG. 21.

DESCRIPTION OF THE PREFERRED EMBODIMENTS

FIG. 1 is a timing chart for explaining the principles of a concentration measuring method of the present invention. In the present invention, a concentration measuring device for embodying the concentration measuring method of the present invention is activated, and a signal of an absolute value of a background light in a space where the device is placed is read as a difference between outputs S20 and S10 (absolute value output X).

Next, light from a light source 1 that emits light (L$\lambda$1) having a first wavelength is received by a light-receiving sensor, and a differential output signal (G$\Delta$1) of a difference between outputs S30 and S40 is read (output as a sum of the background light and the light of the light source 1).

Next, light from a light source 2 that emits a light (L$\lambda$2) having a second wavelength is received by the same light-receiving sensor, and a differential output signal (G$\Delta$2) of a difference between outputs S50 and S60 is read (output as a sum of the background light and the light of the light source 2).

Measurement data can be calibrated using the absolute value output X, even if a change occurs in an amount of light of the light source, an absorbance of an object to be measured as a result of a temperature change, or the like.

With the light-receiving signals from the light sources 1, 2 output as differential output signals, noise of a circuit system can be removed, making it possible to achieve detection with high accuracy, even if the concentration is weak.

In FIG. 1, "↑" indicates the output timing of the light-receiving sensor. While in principle the output timing "↑" includes a rise start point (t1) and a fall start point (t2) of the output of the light-receiving sensor, the output timing "↑" in FIG. 1 is the timing between the rise start point (t1) and the fall start point (t2). This is because, when one measurement ends, an electronic circuit is partially reset for the next measurement. That is, a measurement period and a reset period may overlap due to a time lag in the circuit and thus, to reliably avoid effects therefrom, the output timing "↑" is the timing between the rise start time (t1) and the fall start time (t2).

FIG. 2 is a block diagram of a configuration example of an optical concentration measuring system 100 serving as a preferred embodiment that embodies the concentration measuring method of the present invention.

The optical concentration measuring system 100 comprises a light source portion 101, a light-focusing optical portion 102, a light-receiving sensor portion 106, a differential signal forming portion 108, a signal storage/processing portion 110, a display unit 112, a control unit 113, and an operation portion 114.

The optical concentration measuring system 100 illustrated in FIG. 2 comprises an optical gas concentration measuring sub-system 100-1 and a control/operation sub-system 100-2.

The optical gas concentration measuring sub-system 100-1 comprises an optical gas concentration measuring device 100-3.

The optical concentration measuring sub-system 100-1 comprises the light source portion 101, the light-focusing optical portion 102, the light-receiving sensor portion 106, the differential signal forming portion 108, the signal storage/processing portion 110, and the display unit 112.

The control/operation sub-system 100-2 comprises the control unit 113 and the operation portion 114.

An object 104 to be measured, subject to concentration measurement of a preferred chemical component, is arranged in a predetermined position between the light-focusing optical portion 102 and the light-receiving sensor portion 106.

While the light source portion 101 illustrated in FIG. 2 comprises two light sources including a light source 101a that emits the light (L$\lambda$1) having the first wavelength and a light source 101b that emits the light (L$\lambda$2) having the second wavelength, the present invention is not limited thereto, allowing a single light source that emits the light (L$\lambda$1) having the first wavelength and the light (L$\lambda$2) having the second wavelength.

A light-emitting portion capable of irradiating light having two or more different wavelengths such as described above may comprise two or more light-emitting elements, each capable of irradiating light having one type of wavelength. Furthermore, the light-emitting portion preferably comprises at least one light-emitting element capable of irradiating light having two or more different wavelengths (multiple wavelength light-emitting element). This decreases the number of light-emitting elements arranged in the device interior, making it possible to reduce the size of the device.

When two light sources are adopted, disposing the two light sources as close to each other as possible so that each light can be irradiated on substantially the same optical axis increases the accuracy of the measured value, and is thus preferred.

When a single light source is adopted, the light (L$\lambda$1) and the light (L$\lambda$2) are selectively separated by means such as a wavelength selecting optical filter prior to being irradiated onto the object 104 to be measured.

When the lights (L$\lambda$1, L$\lambda$2) having the two wavelengths are irradiated using a single light source, the device is designed so that the light having the applicable wavelength is irradiated in accordance with an irradiation timing using an optical wavelength selecting filter such as a spectrum filter.

While the light (L$\lambda$1) having the first wavelength and the light (L$\lambda$2) having the second wavelength may each be light having a single wavelength, adoption of light having multiple wavelengths, each having a bandwidth for a wavelength, is preferred, taking into consideration ease of acquisition of the light source, such as an LED, and cost. Such light preferably has a center wavelength (wavelength with a peak intensity) of $\lambda$1 or $\lambda$2.

In the present invention, the light (L$\lambda$1) is light having a wavelength that has an absorbability with respect to a chemical component subject to concentration measurement. In contrast, the light (L$\lambda$2) is a light having a wavelength that has no or substantially no light absorbability with respect to the chemical component, or an absorbability with respect to the chemical component that is relatively lower than that of the light (L$\lambda$1).

In the present invention, a light such as the light (L$\lambda$2) is preferably adopted since measurement accuracy increases when there is no absorbability with respect to the chemical component or to the extent the absorbability differs from that of the light (L$\lambda$1).

When the concentrations of a plurality of chemical components are measured using the same object to be measured, the light (L$\lambda$1) is prepared in a quantity equivalent to the number of chemical components to be measured. That is, given N as the number of chemical components, the light (L$\lambda$1) is prepared in a quantity of n (L$\lambda$1$n$, where n is a positive integer). Among the lights (L$\lambda$1$n$, where n is a positive integer), the light selected as applicable is the light having a wavelength or a wavelength range that exhibits an absorbability with respect to the one chemical component only and no or substantially no absorbability with respect to any other chemical component. For example, when glucose and hemoglobin are measured using the same object to be measured, light (L$\lambda$11) that exhibits absorbability with respect to glucose but not with respect to hemoglobin, and light (L$\lambda$12) that does not exhibit absorbability with respect to glucose but does with respect to hemoglobin are selected.

For the light (L$\lambda$2), light that exhibits no or substantially no absorbability with respect to either chemical component is selected.

As the light source of the light source portion, needless to say, a light source that emits light according to these conditions is selected and used.

The light (L$\lambda$1) and the light (L$\lambda$2) are irradiated onto the object 104 to be measured in accordance with a time-sharing method.

The light (L$\lambda$1) and the light (L$\lambda$2) are preferably irradiated onto the same optical axis or substantially the same optical axis when irradiated onto the object 104 to be measured. That is, even when a chemical component subject to concentration measurement has a spotted distribution or an uneven distribution spatially or temporally in the object 104 to be measured, when the positions in which the light (L$\lambda$1) and the light (L$\lambda$2) pass through the object 104 to be measured are the same or substantially the same, the measurement period is, at the same time, extremely short, resulting in the advantage of achieving a highly accurate measurement minimally affected by measurement errors.

An irradiated light 103 formed by the light (L$\lambda$1) or the light (L$\lambda$2) is irradiated onto the object 104 to be measured and, as a result, a transmitted light 105 exits from the exact opposite side of the object 104 to be measured.

The transmitted light 105 enters a light-receiving surface of a light-receiving sensor located in the light-receiving sensor portion 106.

The light-receiving sensor portion 106 outputs an electric signal 107 in response to the received light.

The signal 107 is either a signal 107a based on the light (L$\lambda$1) or a signal 107b based on the light (L$\lambda$2).

The signal 107a and the signal 107b are input to the differential signal forming portion 108 either sequentially based on a set time difference or simultaneously.

When input based on a set time difference, the signal input first may, depending on the case, be held for a predetermined period in a predetermined circuit inside the differential signal forming portion 108 in accordance with a timing for forming the differential signal.

A differential output signal 109 output from the differential signal forming portion 108 in accordance with the input of the signal 107 is transferred to the signal storage/processing portion 110 and stored/processed so as to output an output signal 111.

The output signal 111 is transferred to the display unit 112. The display unit 112 that received the output signal 111 displays a concentration display of the measured chemical component on a display screen of the display unit 112 as a value corresponding to the output signal 111.

The above series of processes is controlled by the control unit 113 in accordance with instructions from the operation portion 114.

The light-receiving sensor constituting the light-receiving sensor portion 106 may be a single element such as a photodiode, or a line sensor or area sensor in which a predetermined number of light-receiving pixels is one-dimensionally or two-dimensionally disposed, respectively.

When the chemical component to be measured is not uniform in the object 104 to be measured, a measurement error resulting from positional dependency may decrease the measurement accuracy, and thus adoption of a line sensor or an area sensor is preferred. In particular, adoption of an area sensor that has a light-receiving surface having a size that covers an exiting surface from which the transmitted light 105 exits, orthogonal to the optical axis of the object 104 to be measured, can significantly increase measurement accuracy, and is thus preferred.

While the light (L$\lambda$1) and the light (L$\lambda$2) have each been described using a light having a single wavelength, the wavelength is not necessarily limited thereto in the present invention, and the wavelength may have a bandwidth (wavelength range). That is, in the present invention, a luminous flux having a predetermined wavelength range may be used.

Next, an example of actual concentration measurement using the system 100 of FIG. 2 will be described on the basis of FIGS. 3 and 4. FIG. 3 is a flowchart for explaining a preferred embodiment of the concentration measuring method of the present invention.

When a button switch of the operation portion 114, or the like, for starting measurement is pressed, concentration measurement is started (step 201).

In step 202, the existence or absence of the specimen 104 serving as the object to be measured, including if the specimen 104 is appropriately placed in a predetermined position, is determined. When it is determined that the specimen 104 has been appropriately placed, the first light (L$\lambda$1) and the second light (L$\lambda$2) necessary and appropriate for measuring the concentration of a chemical component to be measured in the specimen 104 are selected in step 202.

Selection of the first light (L$\lambda$1) and the second light (L$\lambda$2) is made by setting the light source 101a for the first light (L$\lambda$1) and the light source 101b for the second light (L$\lambda$2) in predetermined positions in the optical concentration measuring system 100, or dispersing the light using a spectroscope.

When selection is based on the establishment of a light source, selection of the first light (L$\lambda$1) and the second light (L$\lambda$2) can be made in advance from an absorption spectrum of the chemical component to be measured in the specimen 104, allowing step 203 to be performed before step 201.

Next, in step 204, acquisition of an analytical curve for deriving the concentration value of the chemical component to be measured based on measurement data is started.

The analytical curve can be acquired by reading the data of an analytical curve stored in advance in a storage portion of the optical concentration measuring system 100, or by creating a new analytical curve as described in FIG. 5.

Once acquisition of the analytical curve is complete, measurement of the specimen 104 is started as indicated in step 206.

When measurement is started, the first light (L$\lambda$1) and the second light (L$\lambda$2) are irradiated onto the specimen 104 for a predetermined period by time-sharing at a predetermined interval.

The first light (L$\lambda$1) and the second light (L$\lambda$2) that passed through the specimen 104 are received by a light-receiving sensor set in the light-receiving sensor portion 106 (step 207).

When the light-receiving sensor receives each transmitted light of the first light (L$\lambda$1) and the second light (L$\lambda$2) by time-sharing, an output signal of a size corresponding to the amount of received light is output each time light is received. In accordance with this output signal, "$-\log(1-\Delta T)$" is calculated (step 208).

Next, in step 209, whether or not "$-\log(1-\Delta T)$" is in the range of the analytical curve is determined.

If "$-\log(1-\Delta T)$" is within the range of the analytical curve, the concentration of the targeted chemical component in the specimen 104 is derived on the basis of the analytical curve data (step 210).

Next, in step 209, whether or not "$-\log(1-\Delta T)$" is in the range of the analytical curve is determined.

If "$-\log(1-\Delta T)$" is within the range of the analytical curve, the concentration of the targeted chemical component in the specimen 104 is derived on the basis of the analytical curve data (step 210).

FIG. 4 is a timing chart for explaining a signal output timing of the example in FIG. 3. That is, FIG. 4 is a timing chart showing the time responses of an output OUT1 of the first light source 101a, an output OUT2 of the second light source 101b, an output OUT3 of the light-receiving sensor, an output OUT4 of the differential signal, and a gas concentration GC.

Here, "output of the light source" is the amount of light emitted during the period that the light is on (hereinafter "ON period") and, when the light has high directivity, is substantially equivalent to the amount of light received by the light-receiving sensor.

In the present invention, each light from the light sources 101a, 101b can be focused by the light-focusing optical portion 102 as illustrated in FIG. 7 to 9, or a branch-type optical fiber 801 can be adopted as illustrated in FIG. 10, and thus as long as the light sources 101a, 101b are arranged by bringing an emitting surface of the light sources 101a, 101b near or in contact with an incident surface of the light-focusing optical portion 102 or an incident surface of the branch-type optical fiber 801, it is possible to make the amount of light emitted during the ON period of each of the light sources 101a, 101b close to or substantially equivalent to the amount of light received by the light-receiving sensor.

The gas concentration GC can, for example, be measured as a change in concentration of the target gas obtained by detecting an output signal (differential signal output OUT4) at timings T1 to T4 illustrated in FIG. 4 and deriving the value from the detected output signal value and the analytical curve acquired in advance.

FIG. 4 illustrates a state of the gas concentration GC increasing in stages over time.

When the output OUT1 of the first light source and the output OUT2 of the second light source are output on the same axis at mutually predetermined and repeated intervals at timings such as illustrated in FIG. 4, the gas to be measured does not exist before timing T1, and thus the output OUT3 of the light-receiving sensor is output as pulses S11, S21 having the same size.

During the period between timings T1 and T2, the period between timings T2 and T3, and the period between the timings T3 and T4, the pulses S12, S22, S13, S23, S14, S24 are output. While the sizes of the pulses S12, S13, S14 are the same as the size of the pulse S11, the sizes of the pulses S22, S23, S24 decrease in stages in accordance with the level of light absorption of the gas to be measured.

That is, because the light from the second light source is absorbed in the gas to be measured and the amount of light received by the light-receiving sensor gradually decreases in accordance with the gas concentration, the sizes of the pulses S22, S23, S24 decrease in stages in accordance with the level of concentration of the gas to be measured.

FIG. 5 explains an example of a method for acquiring an analytical curve in advance, prior to measurement of the gas concentration. FIG. 5 is a flowchart for finding the analytical curve.

To acquire the analytical curve, an analytical curve acquiring device is used.

When acquisition of the analytical curve is started (step ST1), whether or not an optical measuring cell has been prepared is determined in step ST2.

Once the optical measuring cell has been prepared, the flow proceeds to step ST3. In step ST3, whether or not a predetermined carrier gas has been introduced into the cell interior in a predetermined unit amount is determined.

When it is determined that the predetermined carrier gas has been introduced into the cell interior in a predetermined unit amount, the flow proceeds to step ST4.

This step of determining whether or not the carrier gas has been introduced may be omitted, or the step may be changed to a step for determining if the cell interior has reached a predetermined degree of vacuum. This determination of whether the cell interior has reached a predetermined degree of vacuum may be omitted as well.

In either case, the cell interior needs to be cleaned before proceeding to step ST4 in order to acquire a more accurate analytical curve.

In step ST4, a plurality of gases subject to concentration measurement is sequentially introduced into the cell, and the absorbance of the gas of each concentration is measured.

Once measurement is completed, the flow proceeds to step ST5.

In step ST5, the analytical curve is created on the bases of the absorbance measurement data.

FIG. 6 illustrates an example of an analytical curve created in this way.

FIG. 6 is a graph showing a relationship between the gas concentration GC and "$-\log(1-\Delta T)$."

Once the analytical curve is created, the flow can transition to concentration measurement of the specimen.

Next, a preferred embodiment according to the present invention illustrated in FIGS. 7 to 10 will be described. In FIGS. 7 to 10, the same components as those in FIG. 2 will be denoted using the same reference numerals.

FIG. 7 is an explanatory schematic configuration view for explaining a main component 100a of a preferred embodiment of the optical concentration measuring system that embodies the concentration measuring method of the present invention. FIG. 7 is an example of concentration measurement by transmitted light.

In a main component 500, the light source portion comprises the first light source 101a that emits the first light (L$\lambda$1) and the second light source 101b that emits the second light (L$\lambda$2).

The first light (L$\lambda$1) emitted from the first light source 101a is focused on the optical axis by the light-focusing optical portion 102, passed along the optical axis as an irradiated light 103a, and irradiated onto the object 104 to be measured. The amount of the irradiated light 103a not absorbed in the object 104 to be measured exits the object 104 to be measured as a transmitted light 105a.

The transmitted light 105a enters the light-receiving surface of the light-receiving sensor portion 106.

When the transmitted light 105a is received by the light-receiving sensor portion 106, the electric signal 107 photoelectrically converted in accordance with the amount of the transmitted light 105a is output from the light-receiving sensor portion 106.

The signal 107 output from the light-receiving sensor portion 106 is input to the differential signal forming portion 108 configured by a differential signal forming circuit.

The second light (L$\lambda$2) emitted from the second light source 101b is passed along the optical axis as an irradiated light 103b and irradiated onto the object 104 to be measured in the same way as the first light (L$\lambda$1), and a transmitted light 105b exits the object 104 to be measured accordingly.

In the case of the second light (L$\lambda$2), the light is either not absorbed in the object 104 to be measured, or absorbed with a low absorbability compared to the first light (L$\lambda$1). Thus, the amounts of the irradiated light 103b and the transmitted light 105b are either the same or substantially the same, or the difference thereof is less than the difference between the irradiated light 103a and the transmitted light 105a.

FIG. 8 is an explanatory schematic configuration view for explaining main components of another preferred embodiment of the optical concentration measuring system that embodies the concentration measuring method of the present invention. Except for the fact that FIG. 8 is an example of measurement by reflected light while FIG. 7 is an example of measurement by transmitted light, the example in FIG. 8 is the same as that in FIG. 7, and thus a detailed description thereof will be omitted.

FIG. 9 is an explanatory schematic configuration view for explaining main components of yet another preferred embodiment of the optical concentration measuring system that embodies the concentration measuring method of the present invention.

Except for the fact that FIG. 9 is an example of measurement by scattered light while FIG. 7 is an example of measurement by transmitted light, the example in FIG. 9 is the same as that in FIG. 7, and thus a detailed description thereof will be omitted.

FIG. 10 is an explanatory schematic configuration view for explaining a main component of yet another preferred embodiment of the optical concentration measuring system that embodies the concentration measuring method of the present invention. Except for the fact that FIG. 10 adopts a branch-type optical fiber 801 for the light-focusing optical portion 102 in the example in FIG. 7, the example in FIG. 10 is the same as that in FIG. 7, and thus a detailed description thereof will be omitted.

FIG. 11 illustrates a circuit diagram for explaining a preferred example of the differential signal forming portion adopted in the present invention.

A differential signal forming portion 900 comprises a (charge) integrating amplifier 902, a sample/hold circuit 903, and a differential amplifier 904.

When the transmitted light, reflected light, or scattered light produced upon irradiation of light having a predetermined wavelength for concentration measurement onto the object 104 to be measured subject to concentration measurement, such as a fruit or a vegetable, is received by a photodiode 901 for light reception, an electric signal P1 corresponding to the amount of received light is output from the photodiode 901. The electric signal P1 is input to the integrating amplifier 902.

The integrating amplifier 902 is provided for sensitivity enhancement so as to allow measurement down to subtle changes in gas concentration of the specimen 107.

The output signal of the integrating amplifier 902 is input to the sample/hold circuit 903.

A sampled/held analog signal is input to the differential amplifier 904.

Gas Concentration Measurement Example Embodying Present Invention

Next, an example that embodies the present invention will be described using a gas concentration measurement example.

A preferred embodiment of the concentration measuring method for measuring concentration by using a plurality of lights having different wavelengths and irradiating the plurality of lights by time-sharing will now be described.

In the following, a preferred embodiment of a gas concentration measurement example that uses transmitted light for measurement will be primarily described.

Cases where reflected light or scattered light is used for measurement rather than transmitted light, needless to say, also fall into the category of the present invention, and are naturally within the technical field.

Further, the embodiment described below, needless to say, can be easily developed even in a case where the concentration of a solution or the sugar content of a fruit or a vegetable is measured rather than the concentration of a gas.

To embody the present invention as a gas concentration measuring device, the measuring device may comprise a regular light source, a light-receiving photodiode, electronic circuit components, and the like that are easily acquirable, based on a premise of compatibility with the measurement target, and thus in the following descriptions matters obvious to persons skilled in the art will be omitted and main points will be simplified.

The specimen (object to be measured) is, for example, a gas that flows through a gas pipe.

The gas pipe is provided with an incident surface into which light (a measured light $h\lambda$) used for measurement enters, and an exiting surface from which light, having passed through the gas pipe, exits to the outside.

The incident surface and the exiting surface are made of a material having a transmittance of "1" or substantially "1" with respect to the measured light $h\lambda$.

Regardless of whether the gas that flows through the gas pipe is a single type or a plurality of types of mixtures, the measuring device can measure the concentration of the target gas.

In the following, the case of the single type is described using trimethylgallium (TMGa), for example, as the gas serving as the specimen.

Other examples of the specimen gas type include trimethylindium (TMIn) and titanium tetrachloride (TiCl4).

In the gas concentration measurement of trimethylgallium (TMGa), an LED that emits light (L$\lambda$1) having a center light wavelength of 500 nm is adopted as the first light source 101a, for example, and the light intensity thereof is 1.0 mW/cm$^2$/nm.

An LED that emits light (L$\lambda$2) having a center light wavelength of 230 nm is adopted as the second light source 101b, and the light intensity thereof is 1.0 mW/cm$^2$/nm.

In the present invention, the light (L$\lambda$1) 103a emitted from the first light source 101a and the light (L$\lambda$2) 103b emitted from the second light source 101b are transmitted through the specimen 104 at separate times (by time-sharing), and enter the light-receiving sensor of the light-receiving sensor portion 106. As the light-receiving sensor, a photodiode (S1336-18BQ) manufactured by Hamamatsu Photonics K.K, for example, may be used. The received light sensitivity of the light-receiving sensor in this case is 0.26 A/W at a light wavelength of 500 nm, and 0.13 A/W at a light wavelength of 230 mm.

The output signal 107 of the light-receiving sensor portion 106 is input to the differential signal forming circuit 108, and the output signal 109 is output from the differential signal forming circuit 108 accordingly.

A light source that emits light having an absorbance that changes depending on the concentration of the gas of the specimen 104, and a light source that emits light having an absorbance that does not or substantially does not change depending on the concentration of the gas of the specimen 104 are adopted as the first light source 101a and the second light source 101b, respectively.

While the above gas concentration measurement example has been described using the configuration in FIG. 7 that measures transmitted light, naturally the measurement can be applied to the configuration in FIG. 8 that uses a reflected light and to the configuration in FIG. 9 that uses a scattered light without having to particularly re-describe the details.

Further, while an optical path of the first light source 101a and an optical path of the second light source 101b differ in the object 104 to be measured if the light-focusing optical portion 102 does not exist in the configuration illustrated in FIG. 7, preferably the first light source 101a and the second light source 101b are arranged as close to each other as possible so as to bring the optical paths as close to the same optical path as possible.

Or, the optical paths can be made substantially identical when the branch-type optical fiber 801 is adopted as illustrated in FIG. 10 in place of the light-focusing optical portion 102, and thus adoption of the branch-type optical fiber 801 is preferred.

FIG. 11 is a configuration diagram for explaining a configuration of a preferred example of the differential signal forming circuit.

The differential signal forming circuit 900 illustrated in FIG. 11 is provided with the (charge) integrating amplifier 902 to increase sensitivity so that subtle changes in the gas concentration of the specimen 107 can be measured.

The output signal of the (charge) integrating amplifier 902 is input to the sample/hold circuit 903.

A sampled/held analog signal is input to an analog-digital converter (ADC) 1301.

An optical signal based on the first light source, an optical signal based on the second light source, and a differential signal between these two signals are output from the ADC 1301.

FIG. 4 is a timing chart showing the time responses of the output OUT1 of the first light source 101a, the output OUT2 of the second light source 101b, the output OUT3 of the light-receiving sensor, the output OUT4 of the differential signal, and the gas concentration GC, and this is as previously described.

Here, "output of the light source" is the amount of light emitted during the ON period and, when the light has high directivity, is substantially equivalent to the amount of light received by the light-receiving sensor.

In the present invention, the light from the light sources 101a, 101b can be focused by the light-focusing optical portion 102 as illustrated in FIG. 7 to 9, or the branch-type optical fiber 801 can be adopted as illustrated in FIG. 10, and thus as long as the light sources 101a, 101b are arranged by bringing the emitting surface of the light sources 101a, 101b near or in contact with the incident surface of the light-focusing optical portion 102 or the incident surface of the branch-type optical fiber 801, it is possible to make the amount of light emitted during the ON period of the light sources 101a, 101b close to or substantially equivalent to the amount of light received by the light-receiving sensor.

In general, absorbance is given based on the following formula:

[Formula 1]

$$-\log(I/I_0) = -\log(1-\Delta T) = \alpha K \quad (1)$$

Here, "$I_0$" indicates the intensity of the incident light, "I" indicates the intensity of the transmitted light, and "K" indicates the gas concentration. $\alpha$ is a coefficient and is determined by an optical path length in the specimen 104, a light absorption coefficient of the gas subject to concentration measurement in the specimen 104, and the like.

Further, "ΔT" indicates the absorbance difference. In this embodiment, the optical path lengths are set so that α is substantially 0 for the first light source 101a, and 2.18×10−4/ppm for the second light source 101b. Given "$I_1$" as the intensity of the transmitted light of the light (Lλ1) emitted from the first light source 101a and "$I_2$" as the intensity of the transmitted light of the light (Lλ2) emitted from the second light source 101b, formula (1) can be modified to formula (2) when $I_1$ uses the fact that the transmittance difference with respect to the optical wavelength of the first light source, regardless of gas concentration, is substantially 0.

[Formula 2]

$$-\log(I - \Delta T) = -\log\left(1 - \frac{X}{I_1}\right) = \alpha K \quad (2)$$

Here, "X" is the output value of the differential signal, and is equivalent to "$I_2 - I_1$."

According to this formula, the absorbance of the specimen 104 can be measured with high accuracy using the output OUT1 of the first light source 101a having an absorptivity that changes in accordance with the gas concentration, and the output OUT2 of the second light source 101b having an absorptivity that does not change in accordance with the gas concentration.

Thus, there is no need to measure gas concentrations to create an analytical curve for each measurement using known reference samples.

A gas densitometer can measure changes in absorptivity in a stable manner, even if there are changes in the measurement system, gas temperature, or the like.

Setup is performed so that an integrated charge (1) of the integrating amplifier 902 based on the first light source 101a and the integrating charge (2) of the integrating amplifier 902 based on the second light source 101b when the gas concentration is "0" are equal or substantially equal.

Here, in this embodiment, an integration period (1) during output of the first light source 101a and an integration period (2) during output of the second light source 101b were adjusted so that the charges were 6.1×10−9 C.

The integration period (1) and the integration period (2) of this embodiment were set to 4.0 msec and 2.0 msec, respectively.

FIG. 15 shows a relationship between an absorbance value measured with respect to a gas concentration and a value equivalent to three times a standard deviation of a noise superimposed on the measured signal at this time.

Further, when measurement was made using this charge, the main noise component was confirmed as photon shot noise.

Based on the results, when the charge value is 6.1×10−9 C, the effect of the photon shot noise proportional to the square root of the signal charge became relatively small, making it possible to measure an absorbance difference ΔT up to 5×10−5 with 99% reliability. That is, the gas concentration could be measured to an accuracy of 0.1 ppm.

Further, according to the embodiment of the present invention, output is obtained from a difference between signals based on two lights having different wavelengths, even if the temperature changes, making it possible to cancel an amount of fluctuation in a transmittance that changes according to temperature. Thus, even if there is temperature fluctuation during measurement, stable sensitivity can be achieved with high accuracy.

In the present invention, a communication module for short-range communication, such as WiFi, Bluetooth (registered trademark), or Near Field Communications (NFC), or a communication module for satellite communication is incorporated in the concentration measuring device that embodies the present invention, making it possible to make the concentration measuring device function as an information terminal device on a network. For example, a patient in a hospital can measure his or her blood sugar level in the hospital bed using a non-invasive type of concentration measuring device according to the present invention when it is time for measurement or when instructed by the nurse station, and send the measurement data as is to the nurse station. This makes it possible to alleviate the labor burden of a nurse in terms of making hospital room visits for each patient and taking measurements.

Furthermore, while, for example, a person at risk for diabetes, a person with a low or high blood sugar level being observed and treated at home, or the like may experience an abnormality in blood sugar level while driving a vehicle, become light-headed, no longer be able to drive or find it difficult to drive normally, and cause an accident, such a person can wear a non-invasive type concentration measuring device that comprises a communication function according to the present invention and have the device perform measurements while he or she is driving. In such a case, the device can detect an abnormality in blood sugar level, immediately send the signal indicating abnormality detection to the vehicle that the person is driving, and automatically stop the vehicle in a prompt manner or automatically guide the vehicle to a safe area such as the side of the road and stop the vehicle. Moreover, carried insulin can then be administered and recovery to normalcy achieved.

Further, the data of the abnormal detection can be automatically sent along with necessary personal data of the driver to a family doctor or nearby hospital to request emergency instructions from the hospital.

While FIG. 11 illustrates a preferred example of the differential signal forming circuit in the realization of the present invention, the present invention is not limited thereto, allowing adoption of the differential signal forming circuits illustrated in FIGS. 12 to 14 as preferred examples as well.

In FIGS. 12 to 14, components that fulfill the same functions as those denoted with the reference numerals in FIG. 11 are denoted using the same reference numerals as FIG. 11.

The configuration illustrated in FIG. 12 is the same as that in FIG. 11 except that, in addition to a circuit for a differential signal output 905, a circuit for a pre-differential signal output 1001 has been added.

With the addition of the circuit for the pre-differential signal output 1001, there is the advantage that, compared to the configuration illustrated in FIG. 11, even if fluctuation occurs in the absolute value of absorbance due to temperature change or the like, or temporal fluctuation occurs in the light output of the light source, the amount of these fluctuations can be measured and calibrated.

In the configuration illustrated in FIG. 13, two systems for signal transmission (sample/hold circuits 903a, 903b→differential amplifiers 904a, 904b) and the ADC 1301 are further provided compared to the configuration illustrated in FIG. 12.

This configuration results in the advantage of being able to eliminate the offset of the integrating amplifier compared to that in FIG. 12.

FIG. 14 is an example of a circuit designed in more detail than the example in FIG. 13.

In FIG. 14, an integrating (accumulation) amplifier portion 1401, which is similar to the integrating amplifier 902, and a 1/10× amplifier portion 1402 are provided. In addition, the differential amplifier portions 904a, 904b are each provided with two instrumentation amplifiers for differential output.

Such a configuration results in the advantage of being able to eliminate the offset of the differential amplifiers.

Next, an embodiment of a preferred example of an electronic device comprising the concentration measuring function according to the present invention will be described.

FIGS. 16 and 17 are outline configuration views illustrating an embodiment when the present invention is applied to a mobile terminal device.

FIG. 16 is an outline external view, and FIG. 17 is a block diagram of the internal configuration.

A mobile terminal device 1701 illustrated in FIGS. 16 and 17 comprises a global positioning system (GPS) positioning portion 1703, a calculation processing portion 1704, a storage device 1705, and a display unit 1706.

When the device does not require GPS positioning, the GPS positioning portion 1703 is omitted.

Further, the device may comprise the GPS positioning portion 1703, and an acceleration sensor 1708 and an angular velocity sensor 1709 may be omitted.

Examples of the mobile terminal device 1701 include a mobile electronic device such as a mobile telephone device having a navigation function, a personal digital assistant (PDA), a tablet, or a mobile PC, a wristwatch, and a wearable article such as a scouter, a necklace, a ring, or a bracelet having an electronic device function.

Examples of the mobile terminal device 1701 further include a mobile barometer or altimeter for mountain climbing, and a stopwatch.

The mobile terminal device 1701 is capable of intercommunicating with a device equipped with a transceiver function such as a transceiver base, a transceiver satellite, a NAVI system mounted to a vehicle, a handheld NAVI device, a transceiver connected to a private network system, or other mobile terminal device.

Description is given in the following using the example of a transceiver satellite 1702 as an example of a device equipped with a transceiver function.

The GPS positioning portion 1703 functions as a first current position calculating portion that receives a position information signal sent from the transceiver satellite 1702 and identifies a current position.

The calculation processing portion 1704 receives detection signals of the vertical acceleration sensor 1708 that detects a number of steps and the angular velocity sensor 1709 that detects a direction, autonomously identifies the current position based on these, and executes navigation processing.

The calculation processing portion 1704 comprises a microcomputer, a central processing unit (CPU), and the like.

The storage device 1705 comprises a ROM 1705a that stores a processing program executed by the calculation processing portion 1704 and stores a storage table required in calculation processing, a RAM 1705b that stores calculation results and the like required in calculation processing, and a non-volatile memory 1705c that stores the current position information when navigation processing ends.

The display unit 1706 displays navigation image information output from the calculation processing portion 1704, and comprises a liquid crystal display unit, an organic EL display unit, or the like.

A clock portion 1707 displays a year, month, day, and time corrected using the current time information that indicates the year, month, day, and time output from the GPS positioning portion 1703 when the GPS positioning portion 1703 is activated.

The calculation processing portion 1704 receives the current position information output from the GPS positioning portion 1703, the current time information that indicates the year, month, day, and time output from the clock portion 1707, the acceleration information output from the acceleration sensor 1708 mounted on a hip position of the user that retains the mobile terminal device 1701, the angular velocity information corresponding to the direction of the walking by the user and output from the angular velocity sensor 1709, such as a gyroscope, mounted to the mobile terminal device 1701, and concentration measurement information from a concentration measuring portion 1710 according to the present invention.

The concentration measuring portion 1710 comprises the optical concentration measuring system illustrated in FIG. 7 to 10 or an optical concentration measuring device comprising the same functions as the system, and may be detachably mounted to the mobile terminal device 1701 main body or integrally configured with the main body.

When the concentration measuring portion 1710 is detachably mounted to the main body, the concentration measuring portion 1710 can be removed from the main body at the time of measurement and, for example, brought into contact with the body of a person, allowing measurement of the sugar level in the blood, for example.

The concentration measuring portion 1710 and the main body are both provided with a communication module for short-range communication, such as Wifi, Bluetooth (registered trademark), or NFC, making it possible to perform communication between the concentration measuring portion 1710 and the main body even when the concentration measuring portion 1710 is removed from the main body.

According to the mobile terminal device 1701, concentration measurement data, position information data, and specific individual data stored in the storage device 1705 can be sent to a transmission destination. For example, when an abnormality arises in the blood sugar level of a person while driving a vehicle, a signal indicating the abnormality is sent to the vehicle, causing the vehicle to automatically stop and, at the same time, the concentration measurement data, the position information data, and specific individual data is sent to a family doctor or a hospital in which the family doctor is located, making it possible to request instructions for appropriate treatment from the doctor and, in some cases, promptly dispatch an emergency vehicle.

A communication portion 1711 that performs wireless communication with an external wireless communication device is connected to the calculation processing portion 1704.

The ROM 1705a stores a storage table of position information by region.

Additionally, the ROM 1705a stores an autonomous positioning calculation program for performing autonomous positioning calculations, and a calculation portion selection processing program for selecting either current position information calculated by the GPS positioning portion 1703 or current position information calculated by the autonomous positioning calculation processing performed by the autonomous positioning program.

The storage table of position information by region charts the names of prefectures across the country, the seat names of governments of each prefecture, and the latitude (N) and the longitude (E) of each seat of government.

The calculation processing portion 1704 executes the autonomous positioning calculation processing in accordance with the autonomous positioning calculation program that performs autonomous positioning calculations.

This autonomous positioning calculation processing is started when autonomous calculation processing is selected by the calculation portion selection processing and, once the previous current position identified by the GPS positioning portion 1703 is set as the initial position in the initial state, is executed as timer interrupt processing every predetermined time period (10 msec, for example) with respect to a predetermined main program.

That is, first the autonomous positioning calculation processing reads an angular velocity θv detected by the angular velocity sensor 1709, then integrates the angular velocity θv, calculates the direction θ, and transitions to the next step.

In the next step, the autonomous positioning calculation processing reads a vertical acceleration G detected by the acceleration sensor 1708, calculates a number of steps P from a change pattern of the vertical acceleration G, multiplies a pace width W set in advance by the calculated number of steps P to calculate a moved distance L, updates the current position information on the basis of the calculated direction θ and the moved distance L, displays the updated current position information on the display unit 1706 over map information, ends the timer interrupt processing, and returns to the predetermined main program.

Furthermore, the calculation processing portion 1704 executes calculation portion selection processing that selects either the current position information identified by the GPS positioning portion 1703 in accordance with the calculation portion selection processing program or the current position information identified by the autonomous positioning calculation processing.

According to this calculation portion selection processing, execution is started when the navigation processing is selected on the mobile terminal device 1701 after power ON.

Examples of the mobile terminal device 1701 include a mobile electronic device such as a mobile telephone device having a navigation function, a personal digital assistant (PDA), a tablet, or a mobile PC, a wristwatch, and a wearable article such as a scouter, a necklace, a ring, or a bracelet having an electronic device function.

While in the examples heretofore formation of the differential signal has been exemplified by formation via an electric circuit (hardware) such as a differential circuit and a differential amplification circuit, the present invention is not limited thereto, allowing formation using software of digital calculation processing.

An example of a preferred embodiment will be described using FIG. 18.

The embodiment illustrated in FIG. 18 comprises a differential signal forming portion 1800 and a light-receiving sensor portion 1801.

The differential signal forming portion 1800 comprises an integrated circuit portion 1802, an analog-digital converting (A/D converting) portion (ADC) 1803, and a differential signal forming element portion 1804.

The light-receiving sensor portion 1801 is provided with a photodiode 1805 as a light-receiving sensor for measurement. The integrated circuit portion 1802 is provided with an operational amplifier 1806, a capacitor C1, and a switch SW1.

While the example of the differential signal forming portion 900 illustrated in FIG. 11 forms the differential signal 905 using an analog signal, a differential signal 1809 in the example illustrated in FIG. 18 is formed by performing digital calculation processing after analog-digital conversion (A/D conversion) of a signal 1807 output from the integrated circuit portion 1802.

An output terminal of the photodiode 1805 is electrically connected with an inverting input pin of the operational amplifier 1806.

The non-inverting pin of the operational amplifier 1806 is grounded.

Between the integrated circuit portion 1802 and the ADC 1803, a switch SW2 is provided as necessary and a signal transmission path is formed. The signal transmission path can be formed by electrically connecting the area between the integrated circuit portion 1802 and the ADC 1803.

When two lights (a first light and a second light) differing in wavelength or wavelength band are sequentially irradiated by time-sharing onto an object (specimen) to be measured, the first light and the second light that pass through the object to be measured are sequentially received by the photodiode 1805 by time-sharing in accordance with the irradiation.

When the photodiode 1805 receives the light, an optical charge is produced, and the optical charge is accumulated in the capacitor C1. A signal 1807 of a voltage of a size corresponding to this accumulated charge is output from the integrated circuit portion 1802 when the switch SW2 is turned ON. The signal 1807 is input to the analog-digital conversion means (ADC) 1803, converted into a digital signal, and output from the ADC 1803 as a signal 1808. The digitized signal 1808 is input to the differential signal forming element portion 1804.

Either a signal 1808a corresponding to the first light or a signal 1808b corresponding to a second light, whichever is input first, is temporarily saved in the differential signal forming element portion 1804 interior at least until the signal to be subsequently input is input.

When the signals 1808a, 1808b respectively corresponding to the first light and the second light to be measured are sequentially input to the differential signal forming element portion 1804, differential signal formation processing is implemented in the differential signal forming element portion 1804 on the basis of these signals 1808a, 1808b, and the differential signal 1809 is output from the differential signal forming element portion 1804.

However, when a plurality of light sources is used as the light source for emitting lights having different wavelengths as in the examples in FIGS. 7, 8, 9, and 10, the amount of light may change independently over time for each light source.

This change in the amount of light over time for each light source is not substantial as long as appropriate light sources are selected, and thus generally does not affect the concentration measurement.

However, selecting the light sources requires time and effort, and increases the cost of the product.

Further, in the case of gas concentration measurement or the like, sediment may accumulate on an inner wall surface of a light-receiving window or an inner wall surface of a light-exiting window of a gas flow path arranged in the measured optical path, or each of these inner wall surfaces may become contaminated and, when the amount of transmitted light changes over time, a change may occur in differential output over time even if gas of the same concentration is introduced into the gas flow path, making it no longer possible to achieve an accurate concentration measurement.

In the following, a method that eliminates such concerns and, if time variability occurs in each amount of light of the plurality of light sources, eliminates the effects on concentration measurement is described.

FIG. 19 illustrates an example of such a preferred embodiment.

The embodiment in FIG. 19 is similar to the embodiment in FIG. 10, but further comprises a microcomputer 1901.

Thus, components that are the same as those in FIG. 10 will be denoted using the same reference numerals, and duplicate descriptions thereof will be omitted.

In a gas concentration measuring system 1900, the signal 109 output from the differential signal forming portion 108 is sent to an informing portion 1902 comprising audio output means, display means, and the like, and the informing portion 1902 externally provides information based on the signal 109 by audio, a display, or the like.

The differential signal forming portion 108 and a light source driving portion 1903 are controlled by the microcomputer 1901.

The microcomputer 1901 controls the light source driving portion 1903 so that light emission amounts of light sources 101a, 101b are appropriate in accordance with the differential signal formed by the differential signal forming portion 108.

This control is performed each time a differential signal is formed, and a feedback (FB) signal 1904 output from the light source driving portion 1903 is input to the light source portion 101.

The light emission amounts of the light sources 101a, 101b are controlled in accordance with this FB signal 1904.

In this way, even if the light emission amounts of the light sources 101a, 101b change over time, the light emission amounts are instantly controlled so as to be appropriate.

Further, even if the transmitted amount of light transmitted through a measurement cell changes due to unforeseen circumstances (such as contamination of the light-receiving window or light-exiting window of the cell), it is possible to appropriately perform condensation measurement.

Another embodiment is illustrated using FIGS. 20 to 23.

The embodiment in FIG. 20 is similar to the embodiment in FIG. 12, but further comprises an analog-digital converter (ADC) 2004 and a microcomputer 2005.

Thus, components that are the same as those in FIG. 12 will be denoted using the same reference numerals, and duplicate descriptions thereof will be omitted.

In a concentration measuring system 2000, the differential output 905 output from the differential amplifier 904 is input to the ADC 2004 by activation of a switch SW5.

The differential output 905 input to the ADC 2004 is subjected to A/D conversion inside the ADC 2004. As a result, an output 2009 is output from the ADC 2004 and sent to an informing portion 2007, and information (such as the gas concentration value, for example) based on the output 2009 is provided.

The photodiode 901 receives the measured light that passes through a concentration measurement cell portion 1900a illustrated in FIG. 19, for example.

A microcomputer 2005 issues an instruction signal for adjusting the light emission amount, the integration time of the amount of received light, and the timing of the switches SW1 to SW5 on the basis of the differential output 905 or the output 2009.

When the light emission amount of the light source is adjusted, a microcomputer 2005 sends an instruction signal to a light source driving portion 2006. The light source driving portion 2006 that receives this instruction signal controls a light source portion (not illustrated) so that the light emission amount becomes a predetermined amount in accordance with the instruction signal.

Further, the instruction signal from the microcomputer 2005 may be sent to an integrating amplifier portion 2002, and the ON/OFF timing of the switch SW1 may be controlled to adjust an accumulation time of the capacitor C1 (integration time adjustment of the amount of received light).

Furthermore, the concentration measurement accuracy can be optimized by sending the instruction signal from the microcomputer 2005 to a differential signal forming portion 2001 and adjusting the ON/OFF timing of the switches SW2 to SW5.

Naturally, at this time, overall optimization of the concentration measuring system 2000 can be achieved and measurement accuracy can be further increased by simultaneously sending the instruction signal from the microcomputer 2005 to the integrating amplifier portion 2002 and controlling the ON/OFF timing of the switch SW1 to adjust the accumulation time of the capacitor C1.

Next, a general overview of the steps for measuring concentration using the gas concentration measuring system 2000 in FIG. 20 will be described.

To make the description easy to understand, the description will be given using the concentration measurement of gas as an example for convenience sake.

While the light used includes two lights having different absorbances with respect to the gas subject to concentration measurement, the description will be given with one light as a light not absorbed by the gas subject to concentration measurement.

(1) Adjusting the Light Amount of the Light Source (1-1) A gas, such as Ar or N2, that does not absorb the used light is introduced into a gas concentration measurement cell for measuring the concentration of a predetermined gas.

(1-2) A differential output $V0=Vp(\lambda 2)-Vp(\lambda 1)$ based on the light amounts of the light sources having the optical wavelengths $\lambda 1$ and $\lambda 2$ is measured using a time-sharing method.

Here, LEDs having different optical wavelengths are used as the light sources. The output Vp of the integrating amplifier 902 is expressed by the formula $Vp=(Ipd \times tint)/C1$. Here, Ipd indicates the photodiode (PD) current, tint indicates the integration time of the integrating amplifier, and C1 indicates the capacity at which the feedback of the integrating amplifier is applied.

(1-3) The light emission amount or light integrated amount is adjusted (referred to as light adjustment) so that the differential output of the lights having different wavelengths is a predetermined value or less.

In FIG. 20, the light emission amount of each light source is adjusted to a predetermined value by, for example, sending the instruction signal from the microcomputer 2005 to the light source driving portion 2006.

Here, "predetermined value" refers to the value obtained by subtracting an estimated value of a maximum output differential resulting of specimen gas (the gas subject to concentration measurement) from a maximum range of differential output determined by circuit conditions of the differential signal forming portion 2001.

Using the microcomputer 2005, a voltage (PD driving voltage) for driving the photodiode (PD) 901 is adjusted by sending a feedback (FB) signal to the light source driving portion 2006 in accordance with the differential output 905.

Or, the integration times tint1 and tint2 of the integrating amplifier 902 are adjusted by sending the FB signal to the integrating amplifier portion 2002 in accordance with the differential output 905.

Or, both the PD driving voltage and the integration times of the integrating amplifier 902 may be adjusted.

(1-4) The differential output value V0 after light adjustment is stored in storage means such as semiconductor memory such as RAM (DRAM, ARAM) or ROM, a HDD, or the like. The stored differential output value V0 is read as needed and utilized to calculate concentration when the concentration of the specimen gas is measured.

(1-5) While adjustment of the light amount is executed during the initial period of concentration measurement, adjustment may be performed with every subsequent measurement or intermittently.

(2) Example of Specimen Gas Concentration Measurement (2-1) Specimen gas is introduced into the gas concentration measurement cell.

(2-2) The differential output V (t) is obtained by the time-sharing concentration measuring method of the present invention.

(2-3) V0 is subtracted from V (t) to obtain the differential output change amount Vc (t) corresponding to the concentration of the specimen gas.

$$Vc(t)=V(t)-V0$$

(2-4) The absorbance is obtained from Vc (t).

A detailed flow of the steps for measuring gas concentration is illustrated in FIG. 21.

Next, an example of actual concentration measurement using the system 2000 of FIG. 20 will be described on the basis of FIGS. 21 to 24. For convenience sake, the concentration measurement cell portion 1900a illustrated in FIG. 19 is used as the concentration measurement cell portion. For each of explanation, the light source portion 101 illustrated in FIG. 19 is used as the light source portion.

FIG. 21 is a flowchart for explaining a preferred embodiment of the concentration measuring method of the present invention.

FIG. 21 is similar to the flowchart in FIG. 3, and thus steps having the same meanings as those in FIG. 3 are described using the same reference numerals as FIG. 3.

When a button switch of an operation portion similar to the operation portion 114, or the like, for starting measurement is pressed, concentration measurement is started (step 201).

In step 202, the existence or absence of the specimen 104, including if the object (specimen/concentration measurement cell) 104 to be measured is appropriately placed in a predetermined position, is determined. When it is determined that the specimen 104 has been appropriately placed, the first light (Lλ1) and the second light (Lλ2) necessary and appropriate for measuring the concentration of a chemical component to be measured in the specimen 104 are selected in step 202.

Selection of the first light (Lλ1) and the second light (Lλ2) is made by setting the light source 101a for the first light (Lλ1) and the light source 101b for the second light (Lλ2) in predetermined positions in the optical concentration measuring system 100, or dispersing the light using a spectroscope.

When selection is based on the establishment of a light source, selection of the first light (Lλ1) and the second light (Lλ2) can be made in advance from an absorption spectrum of the chemical component to be measured in the specimen 104, allowing step 203 to be performed before step 201.

Next, in step 204, acquisition of an analytical curve for deriving the concentration value of the chemical component to be measured based on measurement data is started.

The analytical curve can be acquired by reading the data of an analytical curve stored in advance in a storage portion of the optical concentration measuring system 100, or by creating a new analytical curve as described in FIG. 5.

Once acquisition of the analytical curve is complete, measurement of the specimen 104 is started as indicated in step 206.

When measurement is started, introduction of a non-absorbable gas, such as argon (Ar), into the specimen 104 is started (step 2100). Subsequently, adjustment of the light amount as previously described is started (step 2101). Once completion of light amount adjustment is verified (step 2102), the flow proceeds to the next step 2103.

When completion of light amount adjustment is confirmed, introduction of the specimen gas that includes the gas component subject to chemical concentration measurement (gas subject to concentration measurement) into the specimen 104 is started (step 2103).

At the stage when at least the specimen gas has been filled in the specimen 104, the first light (Lλ1) and the second light (Lλ2) are irradiated for a predetermined period onto the specimen 104 by time-sharing at a predetermined interval (part of step 207).

The first light (Lλ1) and the second light (Lλ2) that passed through the specimen 104 are received by a light-receiving sensor (PD 901) set in a light-receiving sensor portion similar to the light-receiving sensor portion 106 illustrated in FIG. 1 (part of step 207).

Next, whether or not output of the light-receiving sensor (PD 901) is within the measurement range is confirmed (step 2104). When output of the light-receiving sensor (PD 901) is confirmed to be within the measurement range, the flow proceeds to step 208.

When output of the light-receiving sensor (PD 901) is not within the measurement range (when "NO"), the flow returns to step 2100 and the process of step 2100 below is executed.

When the light-receiving sensor (PD 901) receives each transmitted light of the first light (Lλ1) and the second light (Lλ2) by time-sharing, an output signal of a size corresponding to the amount of received light is output each time light is received. In accordance with this output signal, "−log (1−ΔT)" is calculated (step 208).

Next, in step 209, whether or not "−log (1−ΔT)" is in the range of the analytical curve is determined.

If "−log (1−ΔT)" is within the range of the analytical curve, the concentration of the targeted chemical component in the specimen 104 is derived on the basis of the analytical curve data (step 210).

FIG. 22 is a diagram illustrating an example of the timing of the gas concentration measuring step, light amount adjustment, and gas introduction illustrated in the flowchart in FIG. 21.

FIG. 23 is a timing chart of the ON/OFF state of light emission of each light source, and the output Vp of the integrating amplifier illustrated in the flowchart in FIG. 21.

The symbols in FIG. 23 have the following meanings:
(a) Gas: Non-absorbable gas (Ar), optical wavelength: λ2
(b) Gas: Non-absorbable gas (Ar), optical wavelength: λ1
(c) Gas: Specimen gas, optical wavelength: λ2
(d) Gas: Specimen gas, optical wavelength: λ1
(e) Gas: Specimen gas, optical wavelength: λ2
(f) Gas: Specimen gas, optical wavelength: λ1
Integrating amplifier output: Vp=(Ipd×tint)/C1
Ipd: PD current
tint: Integrating time
C1: Capacity of the integrating amplifier portion 2002, feedback of the accumulation time adjustment is applied.

"Output of the light source" in the present invention is the amount of light emitted during the ON period and, when the light has high directivity, is substantially equivalent to the amount of light received by the light-receiving sensor.

While the above has been described as a preferred embodiment of the present invention using FIGS. 20 to 23, it is understood that significant amount of the content described in FIGS. 1 to 18 is undeniably applicable to the example described using FIGS. 20 to 23.

For example, the steps can be performed in accordance with the flowchart illustrated in FIG. 5 utilizing an analytical curve acquiring device to acquire the analytical curve.

In the embodiment of the present invention described using FIGS. 19 to 23, the following advantages are expected:
(1) Even if the initial differential output is not zero, gas concentration can be measured with high accuracy.
(2) Differential output is monitored in real time and feedback control is performed, making it possible to measure gas concentration with high accuracy even if the characteristics of the LED (light source) and the transmittance of the optical path change over time.

While the above explanation has been described two types of lights for measurement that have different wavelengths and are irradiated on the object to be measured, the present invention is not limited thereto, allowing three types or more. This point is easily understood by those skilled in the art.

As described above, the concentration measuring method of the present invention has universality, i.e., the ability to be embodied in various forms and modes.

DESCRIPTIONS OF REFERENCE NUMERALS

100 Optical concentration measuring system
100-1 Optical concentration measuring sub-system
100-2 Control/Operation sub-system
100-3 Optical concentration measuring device
101 Light source portion
101a, 101b Light source
102 Light-focusing optical portion
103, 103a, 103b Irradiated light
104 Object to be measured
105, 105a, 105b Transmitted light
106 Light-receiving sensor portion
107, 107a, 107b Electric signal
108 Differential signal forming portion
109 Differential output signal
110 Signal storage/processing portion
111 Output signal
112 Display unit
113 Control unit
114 Operation portion
201 to 211 Step
500, 600, 700, 800 Optical gas concentration measuring system
801 Branch-type optical fiber
801a, 801b Branch optical path
802a, 802b Irradiated light
900, 1000, 1300, 1400 Differential signal forming portion (circuit configuration)
901 Photodiode
902 Integrating amplifier
903, 903a, 903b Sample/Hold circuit
940, 904a, 904b Differential amplifier
905 Differential signal output
906 Pre-differential signal output
1101 Differential signal forming element portion
1301 ADC
1302 Signal output
1401 Integrating amplifier portion
1402 1/10× integrating amplifier portion
1701 Mobile terminal device
1703 GPS positioning portion
1704 Calculation processing portion
1705 Storage device
1706 Display unit
1708 Acceleration sensor
1709 Angular velocity sensor
1800 Differential signal forming portion
1801 Light-receiving sensor portion
1802 Integrated circuit portion
1803 Digital-analog converting portion
1804 Differential signal forming element portion
1805 Photodiode
1806 Operational amplifier
1807, 1808 Signal
1809 Differential signal
Lλ1 Light having a first wavelength
Lλ2 Light having a second wavelength 1900, 2000 Gas concentration measuring system
1900a Concentration measurement cell portion
1901, 2005 Microcomputer
1902 Informing portion
1903, 2006 Light source driving portion
2001 Differential signal forming portion
2002 Integrating amplifier portion
2003 Signal selecting and differential amplifier portion
2004 ADC

What is claimed is:

1. A concentration measuring method for optically measuring a concentration of a predetermined chemical component in an object to be measured, the method comprising the steps of:
irradiating at least light (1) having a first wavelength (λ1) that has an absorbability with respect to the chemical component, and light (2) having a second wavelength (λ2) that has no or substantially no absorbability with respect to the chemical component, or an absorbability that is relatively lower than that of the light (1), from light-emitting unit toward the object to be measured using a time-sharing method;
sequentially receiving the light that is produced by the irradiation and passes through the object to be measured by light-receiving unit;
inputting a first light-receiving signal (1) based on the light (1) and a second light-receiving signal (2) based on the light (2), each produced by the received light into differential signal forming unit;
deriving the concentration of the predetermined chemical component from a measured value based on a differential signal output from the differential signal forming unit in accordance with the input, and data stored in storage unit in advance; and feeding back a feedback signal corresponding to the differential signal to light emission amount control unit for controlling a light emission amount of the light-emitting unit and/or the differential signal forming unit.

2. The concentration measuring method according to claim 1, wherein the object to be measured is in a gas state.

3. The concentration measuring method according claim 1, wherein the object to be measured is in a liquid state.

4. The concentration measuring method according to claim 1, wherein the object to be measured is a fruit or a vegetable.

5. The concentration measuring method according to claim 1, wherein the light-emitting unit comprises a light source that emits the light having the first wavelength and a light source that emits the light having the second wavelength.

6. The concentration measuring method according to claim 1, wherein the light-emitting unit comprises a light source that emits the light having the first wavelength and the light having the second wavelength.

7. The concentration measuring method according to claim 6, wherein irradiation using the time-sharing method is performed by propagating the light through irradiation optical paths in which the optical axes of the emitted light and received light are the same or substantially the same.

8. A concentration measuring method for optically measuring a concentration of a predetermined chemical component in an object to be measured, the method comprising the steps of:

irradiating at least light having a first wavelength that has an absorbability with respect to the chemical component, and light having a second wavelength that has no or substantially no absorbability with respect to the chemical component, or an absorbability that is relatively lower than that of the light having the first wavelength, from a single light-emitting unit toward the object to be measured using a time-sharing method;

sequentially receiving the light that is produced by the irradiation and passes through the object to be measured in a time-sharing manner by a single light-receiving unit;

inputting a first light-receiving signal based on the light having the first wavelength and a second light-receiving signal based on the light having the second wavelength, each produced by the received light, into differential signal forming unit;

deriving the concentration of the predetermined chemical component from a measured value based on an output signal output from the differential signal forming unit in accordance with the input, and data stored in storage unit in advance; and controlling a light emission amount of the light-emitting unit on the basis of a feedback signal corresponding to the differential signal.

9. The concentration measuring method according to claim 8, wherein the object to be measured is in a gas state.

10. The concentration measuring method according claim 8, wherein the object to be measured is in a liquid state.

11. The concentration measuring method according to claim 8, wherein the object to be measured is a fruit or a vegetable.

12. The concentration measuring method according to claim 8, wherein the light-emitting unit comprises a light source that emits the light having the first wavelength and a light source that emits the light having the second wavelength.

13. The concentration measuring method according to claim 8, wherein the light-emitting unit comprises a light source that emits the light having the first wavelength and the light having the second wavelength.

14. A concentration measuring method, comprising the steps of:

irradiating at least light having a first wavelength and light having a second wavelength, each having a different light absorptivity with respect to an object to be measured, onto the object to be measured using a time-sharing method;

sequentially receiving the light of each wavelength that optically passes through the object to be measured as a result of the irradiation of the light of each wavelength, using a common light-receiving sensor;

forming a differential signal between a signal related to the light having the first wavelength and a signal related to the light having the second wavelength output from the light-receiving sensor in accordance with the received light;

deriving a concentration of a chemical component in the object to be measured on the basis of the differential signal; and controlling the amount of light during the emission of at least one of the light having the first wavelength and the light having the second wavelength on the basis of a feedback signal corresponding to the differential signal.

15. The concentration measuring method according to claim 14, wherein the object to be measured is in a gas state.

16. The concentration measuring method according claim 14, wherein the object to be measured is in a liquid state.

17. The concentration measuring method according to claim 14, wherein the object to be measured is a fruit or a vegetable.

18. A concentration measuring method, comprising the steps of:

irradiating at least a first light and a second light, each having a different light absorptivity with respect to an object to be measured, onto the object to be measured using a time-sharing method;

receiving each light that optically passes through the object to be measured by irradiation of each light onto the object to be measured, using a common light-receiving sensor;

forming a differential signal on the basis of a signal related to the first light and a signal related to the second light output from the light-receiving sensor in accordance with the received light;

deriving a concentration of a predetermined chemical component in the object to be measured on the basis of the differential signal; and controlling the amount of light during the emission of at least one of the light having the first wavelength and the light having the second wavelength on the basis of a feedback signal corresponding to the differential signal.

19. A concentration measuring method, comprising the steps of:

irradiating at least light having a first wavelength and light having a second wavelength, each having a different light absorptivity with respect to an object to be measured, onto the object to be measured using a time-sharing method;

receiving the light of each wavelength that optically passes through the object to be measured as a result of the irradiation of the light of each wavelength, using a common light-receiving sensor;

forming a differential signal between a signal related to the light having the first wavelength and a signal related to the light having the second wavelength output from the light-receiving sensor in accordance with the received light;

deriving a concentration of a chemical component in the object to be measured on the basis of the differential signal; and controlling the amount of light during the emission of at least one of the light having the first wavelength and the light having the second wavelength on the basis of a feedback signal corresponding to the differential signal.

20. A concentration measuring method, comprising the steps of:

irradiating at least a first light and a second light, each having a different light absorptivity with respect to an object to be measured, onto the object to be measured using a time-sharing method;

receiving each light that optically passes through the object to be measured by irradiation of each light onto the object to be measured, using a common light-receiving sensor;

forming a differential signal on the basis of a signal related to the first light and a signal related to the second light output from the light-receiving sensor in accordance with the received light;

deriving a concentration of a predetermined chemical component in the object to be measured on the basis of the differential signal; and controlling the amount of light during the emission of at least one of the light having the first wavelength and the light having the second wavelength on the basis of a feedback signal corresponding to the differential signal.

* * * * *

UNITED STATES PATENT AND TRADEMARK OFFICE
CERTIFICATE OF CORRECTION

PATENT NO. : 10,241,034 B2
APPLICATION NO. : 15/506440
DATED : March 26, 2019
INVENTOR(S) : Shigetoshi Sugawa Page 1 of 2

It is certified that error appears in the above-identified patent and that said Letters Patent is hereby corrected as shown below:

On the Title Page

[57] ABSTRACT
Line 5, "object" should read --object with--.

In the Specification

Column 1
Line 64, "[0006]" should be deleted.

Column 8
Line 59, "deriving" should read --¶deriving--.

Column 9
Line 32, "deriving" should read --¶deriving--.

Column 14
Line 41, "based" should read --is based--.

Column 28
Line 34, "convenience sake." should read --convenience.--.

Column 29
Line 41, "convenience sake." should read --convenience.--.

Column 31
Line 20, "significant" should read --a significant--.
Line 36, "been" should be deleted.

Signed and Sealed this
Twelfth Day of November, 2019

Andrei Iancu
*Director of the United States Patent and Trademark Office*

CERTIFICATE OF CORRECTION (continued)
U.S. Pat. No. 10,241,034 B2

Column 32
Line 11, "940," should read --904,--.
Line 36, "1900,2000 Gas" should read --¶1900,2000 Gas--.

In the Claims

Column 32
Line 51, "(1)" and "(λ1)" should be deleted.
Line 53, "(2)" should be deleted.
Line 54, "(λ2)" should be deleted.
Line 56, "(1)" should be deleted; and "from" should read --from a--.
Line 61, "by" should read --by a--.
Line 62, "(1)" should be deleted.
Line 63, "(1)" and "(2)" should be deleted.
Line 64, "(2)" should be deleted.
Line 65, "into" should read --into a--.

Column 33
Line 2, "in" should read --in a--. (second occurrence)
Line 5, "to" should read --to a--.
Line 10, "according" should read --according to--.